(12) United States Patent
Oglaza

(10) Patent No.: US 11,826,085 B2
(45) Date of Patent: Nov. 28, 2023

(54) IMPLANT WITH BLADE FOR DISPLACING OR CUTTING SOFT TISSUE DURING EXPANSION

(71) Applicant: Stryker European Operations Limited, Carrigtwohill (IE)

(72) Inventor: Jean-Francois Oglaza, Portage, MI (US)

(73) Assignee: Stryker European Operations Limited, Carrigtwohill (IE)

( * ) Notice: Subject to any disclaimer, the term of this patent is extended or adjusted under 35 U.S.C. 154(b) by 331 days.

(21) Appl. No.: 17/270,541

(22) PCT Filed: Aug. 29, 2019

(86) PCT No.: PCT/IB2019/057301
§ 371 (c)(1),
(2) Date: Feb. 23, 2021

(87) PCT Pub. No.: WO2020/044289
PCT Pub. Date: Mar. 5, 2020

(65) Prior Publication Data
US 2021/0282826 A1 Sep. 16, 2021

Related U.S. Application Data

(60) Provisional application No. 62/724,768, filed on Aug. 30, 2018.

(51) Int. Cl.
*A61B 17/88* (2006.01)
*A61B 17/16* (2006.01)
(Continued)

(52) U.S. Cl.
CPC ........ *A61B 17/8858* (2013.01); *A61B 17/164* (2013.01); *A61B 2017/00862* (2013.01); *A61F 2/44* (2013.01); *A61F 2002/30579* (2013.01)

(58) Field of Classification Search
CPC .......... A61F 2/44; A61F 2/446; A61F 2/4425; A61F 2/4465; A61F 2/4455; A61F 2/46;
(Continued)

(56) References Cited

U.S. PATENT DOCUMENTS 6,224,604 B1    5/2001   Suddaby
7,846,206 B2   12/2010   Oglaza et al.
(Continued)

FOREIGN PATENT DOCUMENTS

WO    2008044057 A1    4/2008
WO    2010103344 A1    9/2010

OTHER PUBLICATIONS

International Search Report for Application No. PCT/IB2019/057301 dated Dec. 5, 2019, 3 pages.

*Primary Examiner* — Christopher J Beccia
(74) *Attorney, Agent, or Firm* — Howard & Howard Attorneys PLLC

(57) ABSTRACT

An expandable implant for bone restoration. The implant includes a first end element and a second end element. A plate is expandable in a first direction, and a blade expandable in a second direction. A first interconnecting element extends between the plate and at least one of the first and second end elements. A second interconnecting element extends between the blade and at least one of the first and second end elements. When the implant is in a collapsed position, a length of the blade is substantially parallel to the longitudinal axis, and when the blade is in an expanded position, the length of the blade is non-parallel to the longitudinal axis. The blade may include a length extending from a base to a tip, and the tip of the blade is further from the longitudinal axis than the plate when the implant is in the expanded position.

18 Claims, 11 Drawing Sheets

(51) Int. Cl.
*A61B 17/00* (2006.01)
*A61F 2/44* (2006.01)
*A61F 2/30* (2006.01)

(58) Field of Classification Search
CPC ... A61F 2/4611; A61B 17/70; A61B 17/7032; A61B 17/84; A61B 17/844; A61B 17/88
See application file for complete search history.

(56) References Cited

U.S. PATENT DOCUMENTS

| | | |
|---|---|---|
| 8,986,386 B2 | 3/2015 | Oglaza et al. |
| 9,414,933 B2 | 8/2016 | Banouskou |
| 9,579,130 B2 | 2/2017 | Oglaza et al. |
| 2008/0114367 A1 | 5/2008 | Meyer |
| 2015/0282797 A1 | 10/2015 | O'Neil et al. |
| 2016/0242927 A1 | 8/2016 | Seifert et al. |

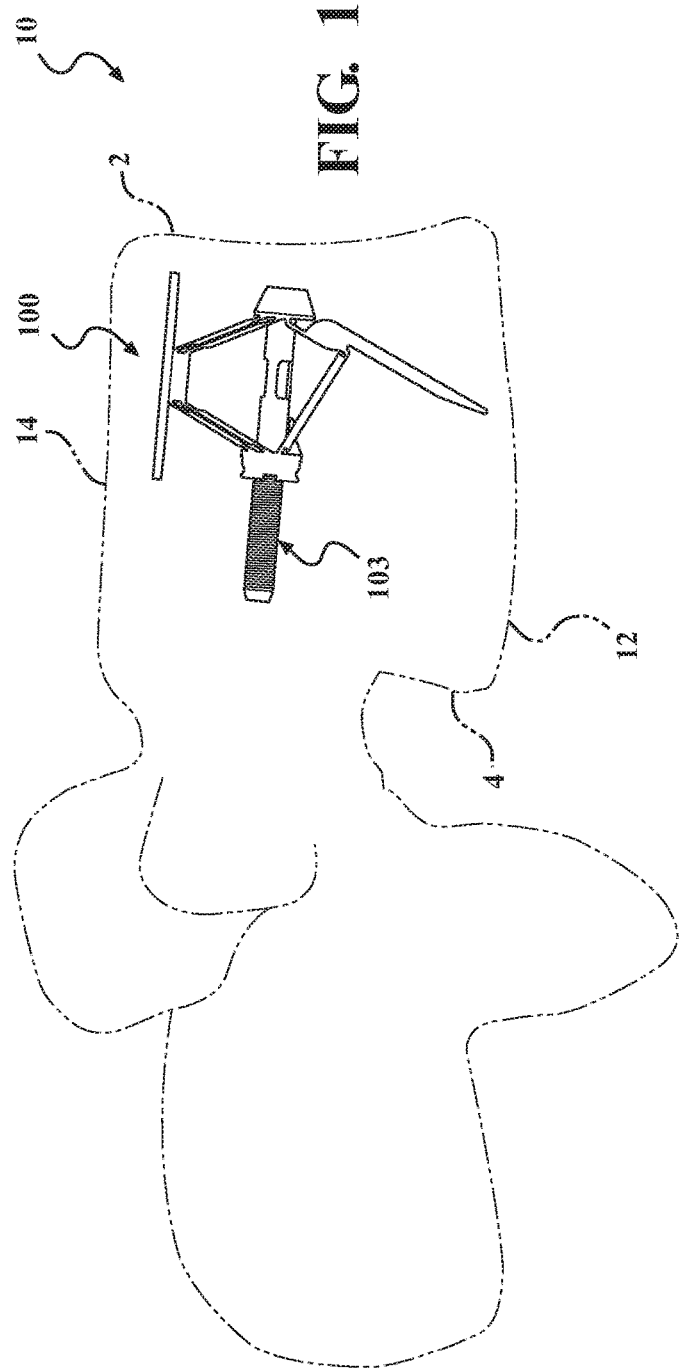
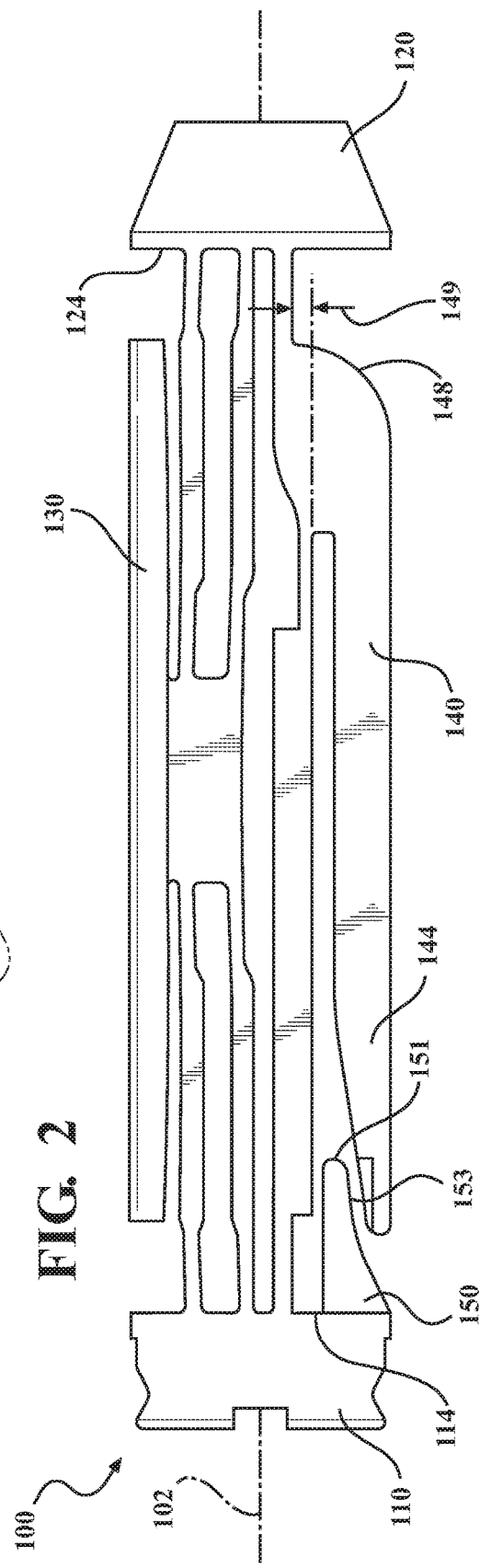

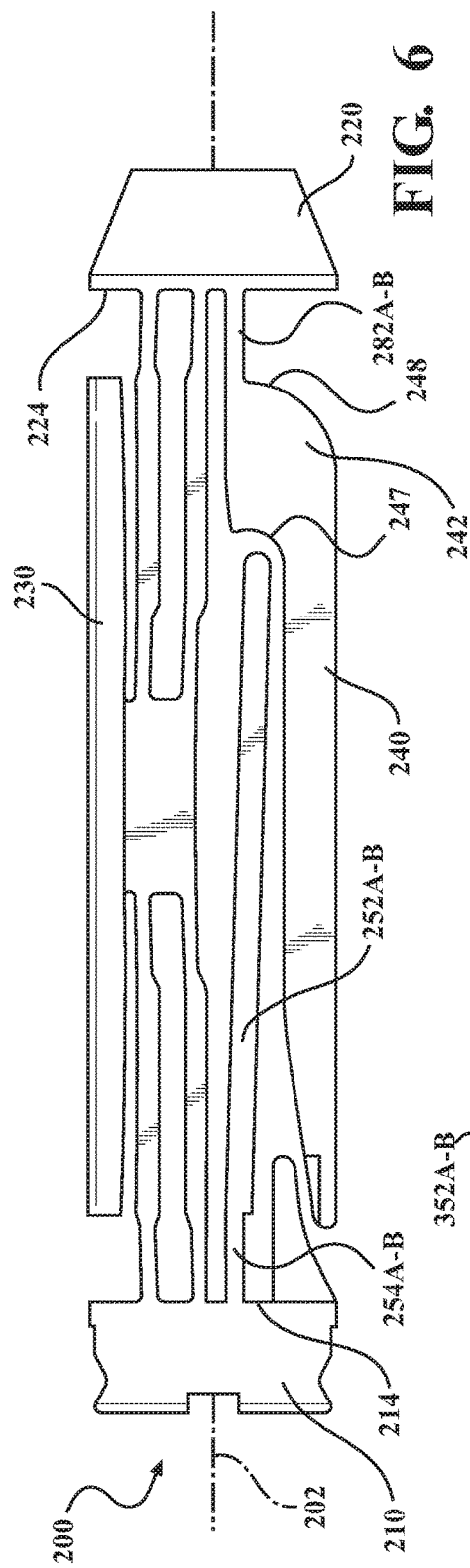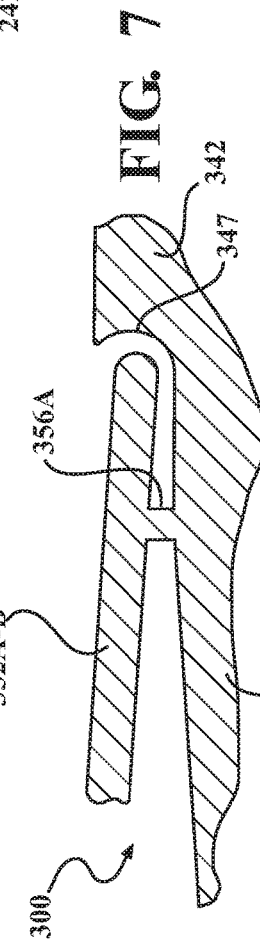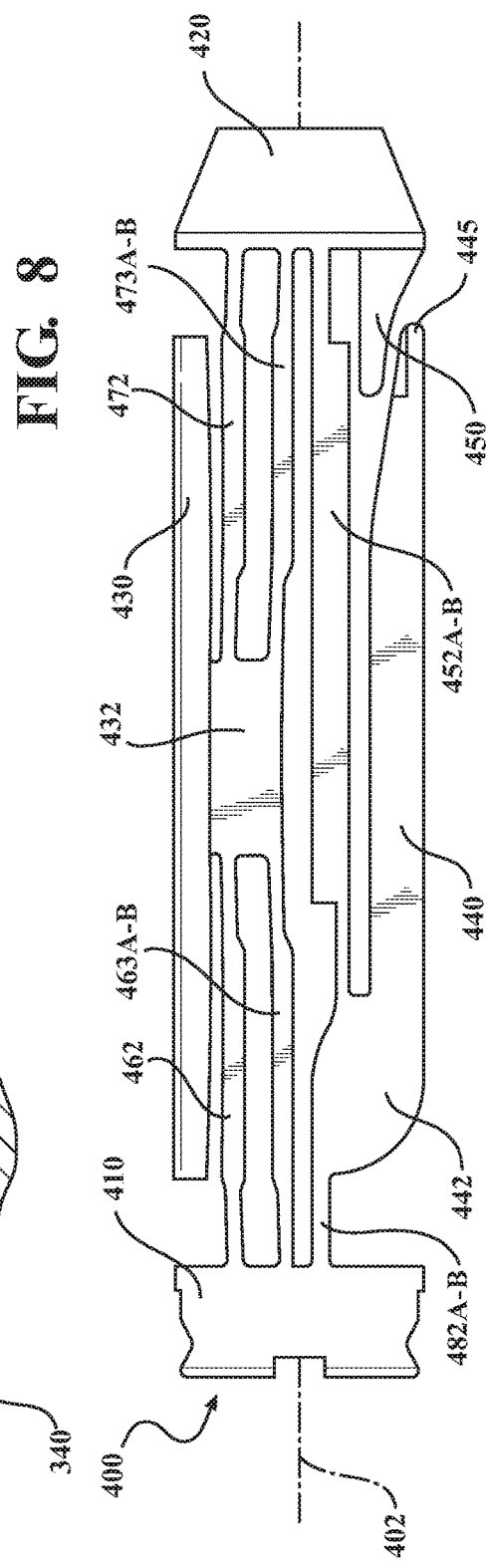

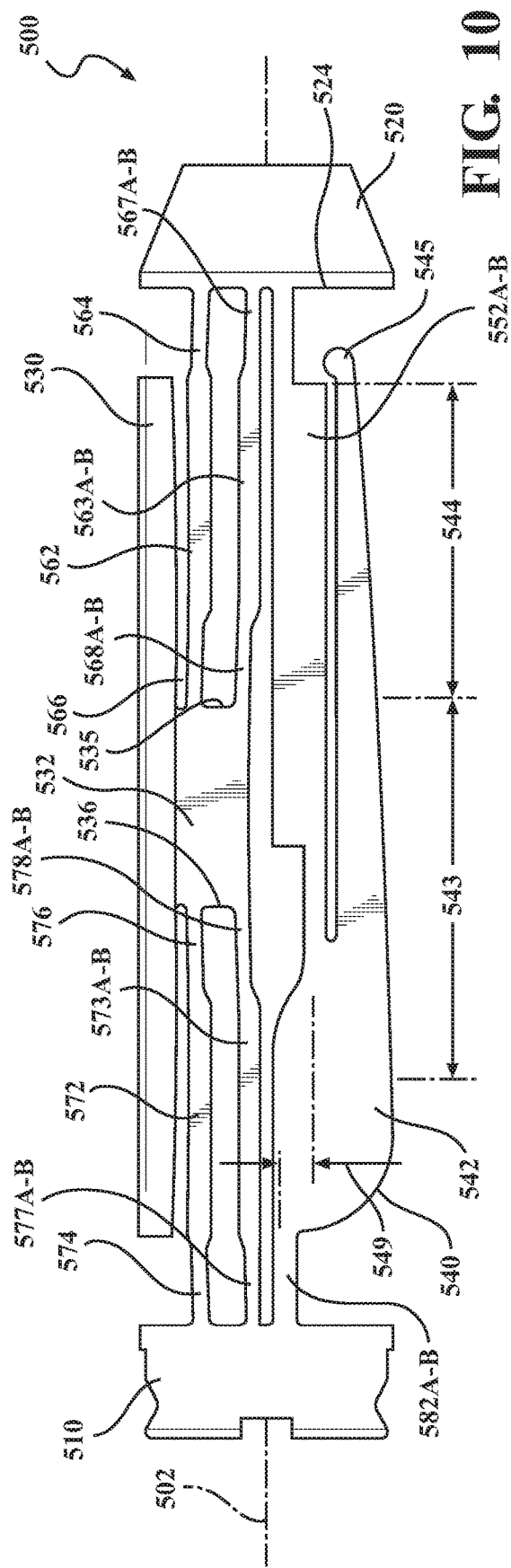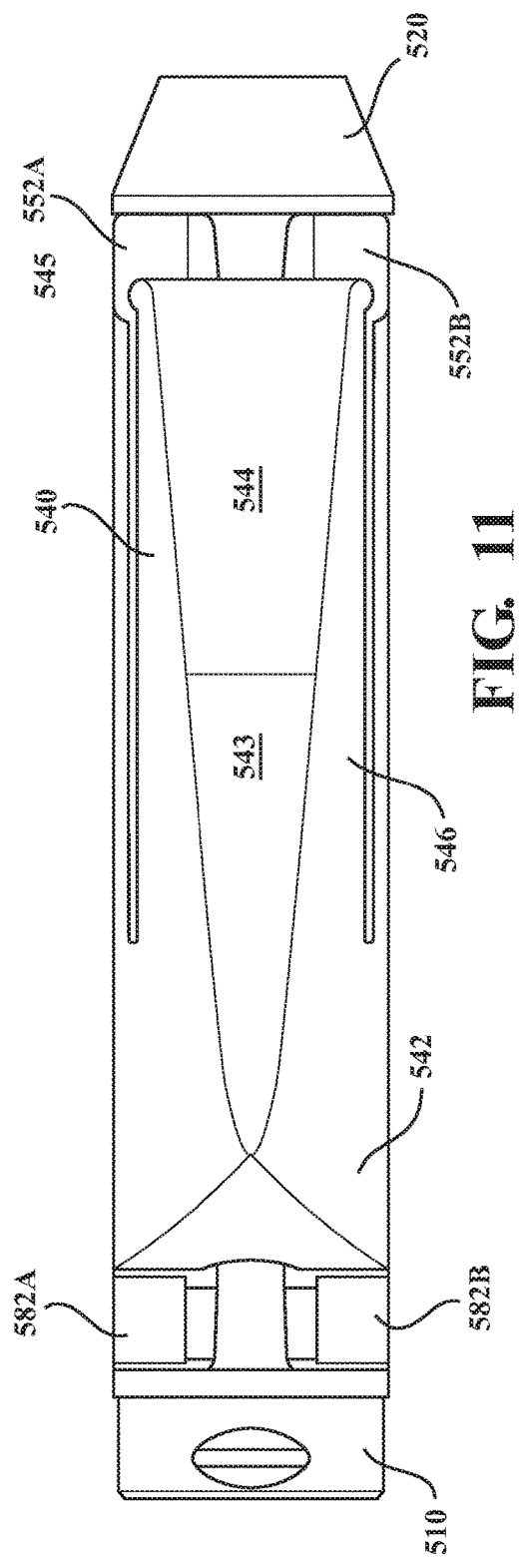

IMPLANT WITH BLADE FOR DISPLACING OR CUTTING SOFT TISSUE DURING EXPANSION

CROSS REFERENCE TO RELATED APPLICATIONS

This is a national stage application of International Patent Application No. PCT/IB2019/057301, filed on Aug. 29, 2019, which claims priority to and all the benefits of U.S. Provisional Application No. 62/724,768, filed Aug. 30, 2018, each of which is hereby incorporated by reference in its entirety.

BACKGROUND

Bone compression fractures may have various causes, such as osteoporosis, which may lead to natural vertebral compression under the weight of an individual. Trauma is another cause, but it is possible that bone compression may result from a variety of causes such as a combination of osteoporosis and trauma. Bone compression may occur in the vertebra, but may also occur in other bones, such as the radius and the femur.

To date, vertebroplasty techniques have been developed in order to address such maladies. However, existing vertebroplasty techniques to effect a vertebral correction, i.e., to restore a vertebra to its original shape, are often either poorly controlled and/or may not provide a structure to ensure that restoration of a bone is preserved over time following surgery.

For example, kyphoplasty involves introduction of an inflatable balloon into the vertebral body followed by the introduction of fluid under pressure into the balloon to force the cortical shell of the vertebra, and in particular the lower and upper vertebral endplates, to correct the shape of the vertebra under the effect of the pressure. Once the osseous cortical shell has been corrected, the balloon is deflated and withdrawn from the vertebra in order to be able to inject cement into the space created by the balloon within the cortical shell, which is intended to impart sufficient mechanical resistance for the correction to last a significant duration in time. Notable disadvantages of kyphoplasty include its onerous procedural steps and the necessity to withdraw the balloon from the patient's body. Furthermore, the expansion of a balloon is poorly controlled because the balloon's volume is multi-directional, which often causes a large pressure to be placed on the cortical shell in less desirable directions. Such large pressures risk bursting of the cortical shell, and in particular, the lateral part of the cortical shell connecting the lower and upper endplates of a vertebra.

In other examples, techniques are employed that utilize implants which are intended to occupy a cavity in a vertebra. Such implants, however, often succumb to collapse within the weeks and months following surgery as they typically do not support a large enough volume within the vertebra. Indeed, the restored height of the vertebra may diminish over time following surgery. Specifically, areas of the bone that are remote from the implant are weak and over time, compress under loading, even with the implant in place. This could occur, for example, in a space below the implant but within the vertebra.

Thus, a need exists for improved implants and related surgical techniques for the repair of collapsed bone structures, particularly improvements to implant structures and obtainable performance from such structures.

SUMMARY

In one aspect, the present disclosure relates to an expandable implant for bone restoration. In one implementation, the implant includes a first end element and a second end element positioned such that a longitudinal axis of the implant passes through a center of the first end element and a center of the second end element. The implant also includes a plate expandable in a first direction and a blade expandable in a second direction. A first interconnecting element extends between the plate and at least one of the first end element and the second end element while a second interconnecting element extends between the blade and at least one of the first end element and the second end element. The structure of the implant is such that, when the implant is in a collapsed position prior to expansion, a length of the blade is substantially parallel to the longitudinal axis, and, when the blade is expanded such that the implant is in an expanded position, the length of the blade is non-parallel to the longitudinal axis.

In one implementation, the plate and the blade are in a single plane in the collapsed position and in the expanded position. In another implementation, when the blade is expanded in the second direction, a tip of the blade moves in an arcuate manner, the tip being remote from an attachment point to the second interconnecting element.

In other implementations, the blade includes a base adjacent to the second interconnecting element and a tip remote from the base, the tip bending when subject to a predetermined load. In one implementation, the blade includes a tapered portion proximal to the tip of the blade. In another implementation, the blade includes a second tapered portion between the first tapered portion and the base, the taper of the second tapered portion being shallower than the taper of the first tapered portion. In still another implementation, the blade includes a recess across a width of the blade, the recess closer to the tip than the base and functioning as a pivot point between portions of the blade on each side of the recess when the tip of the blade is subject to a load. In other implementation, the blade includes a planar bottom surface, the planar bottom surface becoming wider relative to a width of the blade from the base toward the tip.

In one implementation, the tip of the blade is bulbous. In some implementations, each of the first interconnecting element and the second interconnecting element include arms. In particular, the first interconnecting element includes a first arm extending between the plate and the first end element and a second arm extending between the plate and the second end element. Similarly, the second interconnecting element includes a third arm extending between a base of the blade and the first end element and a fourth arm extending between the base and the second end element. In other implementations, when the implant is in a collapsed position, a first axis through a length of the third arm is offset from the longitudinal axis a different amount than a second axis through a length of the fourth arm, the first and second axes being parallel. In yet another implementation, the first axis is offset from the second axis by approximately 0.6 mm. In another implementation, the blade pivots about a location on one of the third arm and fourth arm when the blade expands in the second direction. In some variants, the third arm and the fourth arm each include a longitudinal axis therethrough and an angle between the longitudinal axis through one of the third arm and the fourth arm and the length of the blade changes as the blade expands in the second direction.

In one implementation, the blade is expandable in the second direction such that the tip of the blade is further from the longitudinal axis than the plate. In another implementation, the implant includes a second blade extending directly from one of the first and second end elements that prevents the tip of the first blade from moving toward the longitudinal axis when the implant is expanded. In another implementation, one of the third arm and the fourth arm includes one of a ball and socket for attachment to the other of the ball and socket on the blade. In yet another implementation, the implant includes a frangible material segment connecting one of the third arm and the fourth arm to the blade. In one implementation, the tip of the blade moves away from the longitudinal axis and toward an insertion end of the implant when moving in an arcuate manner during expansion. In another implementation, the tip of the blade moves away from the longitudinal axis and away from an insertion end of the implant when moving in an arcuate manner during expansion.

In another implementation, the present disclosure relates to an implant with a first end element, a second end element, a plate and a blade. The second end element is positioned such that a longitudinal axis of the implant passes through a center of the first end element and a center of the second end element. The plate is attached to both the first end element and the second end element and is oriented such that an axis parallel to the longitudinal axis passes through a length of the plate. The blade includes a base attached to the first end element and the second end element and has a length extending from the base to a tip. The implant is expandable from a collapsed position to an expanded position, the expansion involving the plate and the blade each moving away from the longitudinal axis in different directions. Prior to, during and following expansion, the plate remains substantially parallel to the longitudinal axis. When the implant is in the expanded position, the tip of the blade is further from the longitudinal axis than the plate. Further, a single plane passes through the plate and the blade when the implant is in the collapsed position and when the implant is in the expanded position.

In one implementation, the tip of the blade moves further from the longitudinal axis than the base of the blade when the implant is expanded from the collapsed position to the expanded position. In another implementation, a second axis passes through the length of the blade. In the collapsed position, the second axis is parallel to the longitudinal axis. During expansion, the second axis is at an increasing angle relative to the longitudinal axis. In another implementation, the plate is attached to the first and second end elements via a first attachment point that is equidistant to the first end element and the second end element. Opposite the plate, the blade is attached to the first and second end elements via a second attachment point that is closer to one of the first end element and the second end element. In yet another implementation, the tip is a free end of the blade free of attachment to another element in the collapsed position, the expanded position, and at positions in between.

In yet another aspect, the present disclosure relates to a method of repairing a bone. Initially, an implant is introduced into a bone. The implant includes a first end element, a second end element, a plate and a blade. A longitudinal axis passes through a center of the first end element and a center of the second element. Each of the plate and the blade are attached to both the first end element and the second end element. Further, the implant is expandable from a collapsed position to an expanded position such that the plate and the blade are expandable in different directions. Once the implant is introduced into the bone, an implant expander tool is actuated to cause the first end element of the implant to become closer to the second end element of the implant as the plate and the blade move from the collapsed position to the expanded position. During the actuation, the plate remains substantially parallel to the longitudinal axis and the blade rotates about a pivot axis adjacent to one of the first end element and the second end element. The blade rotation causes a tip of the blade remote from the pivot axis to move in an arcuate manner away from the longitudinal axis. The movement of the plate and the blade toward the expanded position creates a cavity in the bone through displacement of material within the bone, such as cancellous bone.

In one implementation, the method includes injecting cement into the cavity, the cement traversing nearly an entire depth of the bone between opposing cortical surfaces. In one example, the cement flows in between a pair of arms connecting one of the first end element and the second end element with the blade as the cement fills the cavity.

In one implementation, the plate expands a first distance from the longitudinal axis and the tip of the blade expands a second distance from the longitudinal axis. During this expansion, a difference between the second distance and the first distance becomes greater as the implant approaches the expanded position. In another implementation, the blade includes a portion adjacent to the tip that bends when subject to a predetermined load during expansion of the blade. In yet another implementation, the actuating step involves rotating the implant expander tool. In one implementation, the implant undergoes plastic deformation during expansion such that the plate and the blade do not return to the collapsed position. In yet another implementation, the method includes engaging the implant with a retaining element disposed within openings in the first end element and the second end element of the implant. With this engagement, the retaining element prevents the implant from moving toward the collapsed position. In yet another implementation, the expanded position is reached when the plate contacts a first cortical bone surface and the tip of the blade contacts a second cortical bone surface.

In one implementation, a volume of cancellous bone displaced by the blade during rotation of the blade is a function of a length of the blade and a surface area of the blade applying load onto cancellous bone during rotation. In one example, the volume is greater than a second volume of cancellous bone displaced by the plate during expansion of the implant.

BRIEF DESCRIPTION OF THE DRAWINGS

Other objects and advantages of the present disclosure will be apparent from the following detailed description of the present preferred implementations, which description should be considered in conjunction with the accompanying drawings in which like reference indicate similar elements and in which:

FIG. 1 is a perspective view of an implant in an expanded position and disposed within a vertebral body according to one implementation of the disclosure.

FIG. 2 is a side view of the implant of FIG. 1 in a closed position.

FIG. 6 is a side view of an implant according to one implementation of the disclosure in a closed position.

FIG. 7 is a close-up side view of a portion of an implant according to one implementation of the disclosure.

FIG. 8 is a side view of an implant according to one implementation of the disclosure.

FIGS. 10 and 11 are side and bottom views of the implant of FIG. 9.

DETAILED DESCRIPTION

Figure 3:
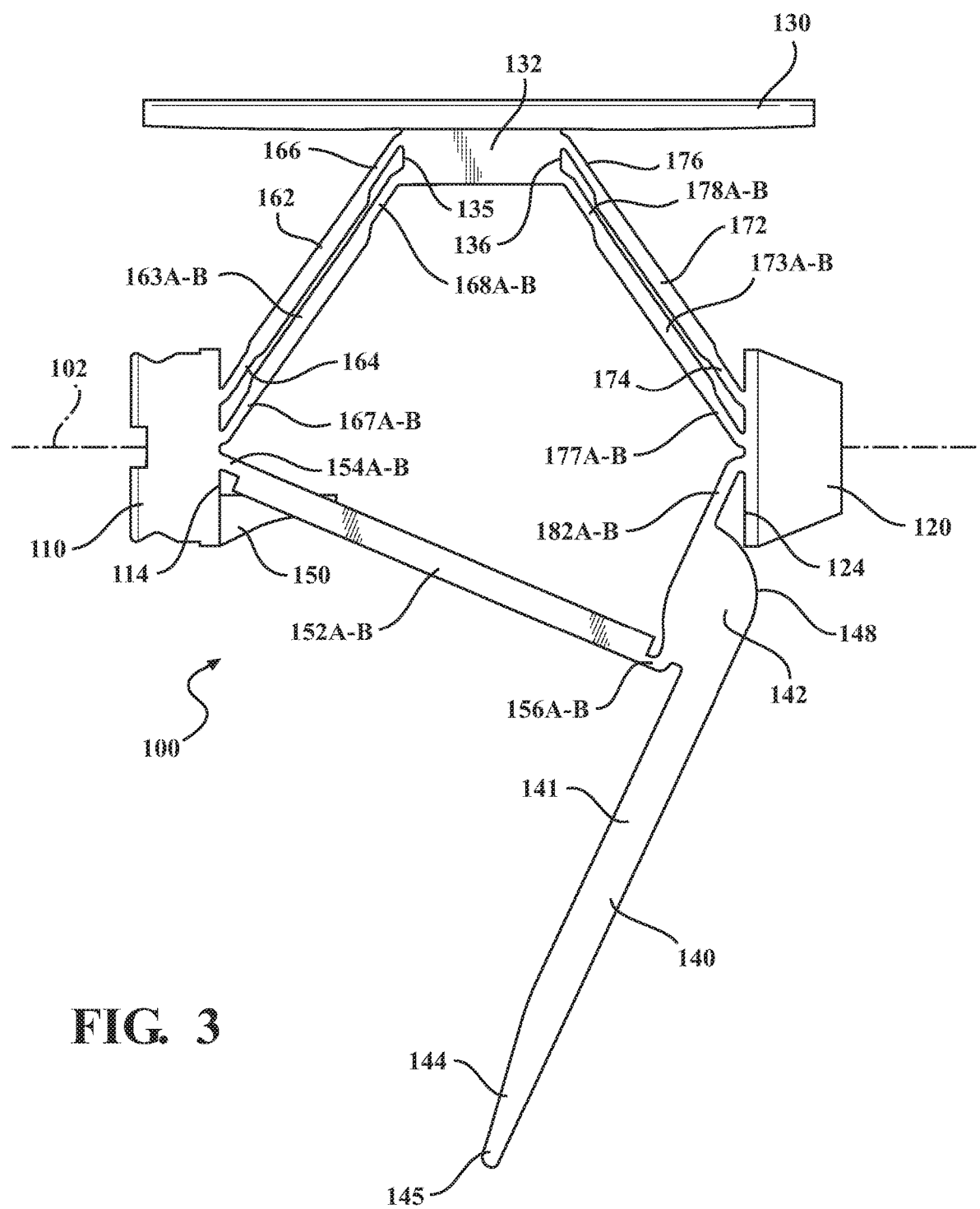
FIG. 3 is a side view of the implant of FIG. 1 in the expanded position.

Throughout the disclosure, an expandable implant is described for use in restoring a collapsed vertebral body of a human or animal through expansion of the implant structure once disposed within the vertebral body. However, although described with particular reference to application within vertebral bodies of the spine, it is also contemplated that the implant of the implementations herein may be used in other areas of the body. For example, the implant may be employed within the cancellous bone in other bones of the body as a restorative measure when such bones have collapsed.

In one aspect, the present disclosure relates to an expandable implant structure to repair a collapsed bone structure. In one implementation, an expandable implant 100 is as shown in FIGS. 1-5. When in an implanted and expanded position, implant 100 lies within a vertebra 10 as shown in FIG. 1. Implant 100 includes a first end element 110, a second end element 120, a plate 130, a blade 140, and several interconnecting elements in the form of arms 162, 172, 152A-B, 182A-B extending between one of the end elements and the plate or blade.

Figure 4:
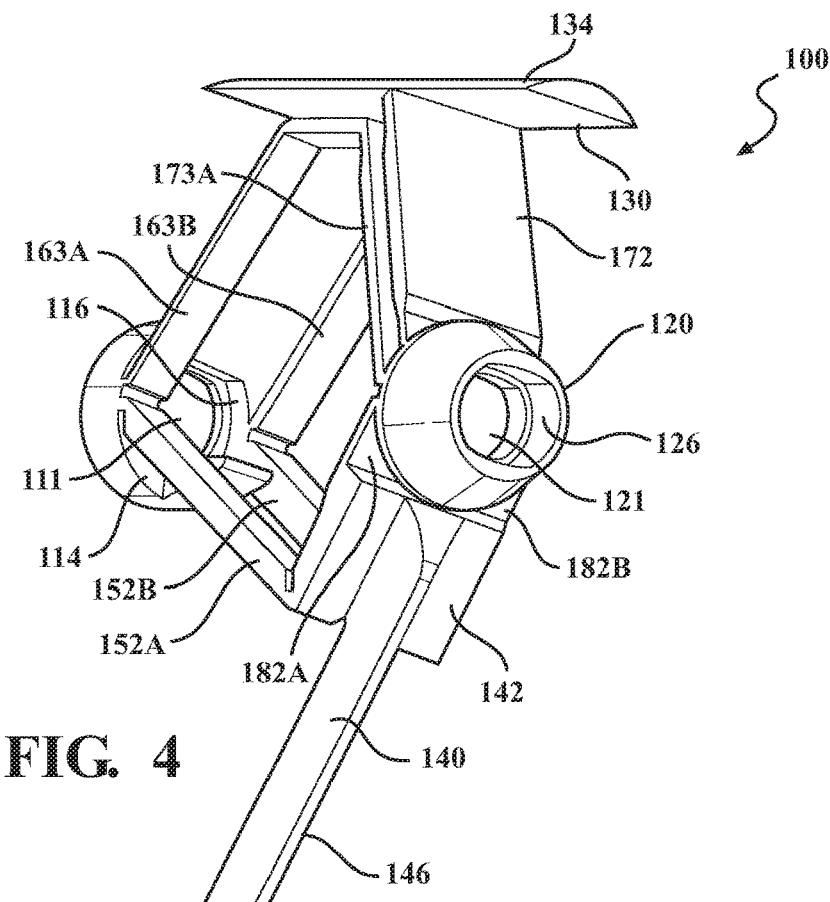
FIG. 4 is a perspective view of the implant of FIG. 1 in the expanded position.

A shape of implant 100 is largely cylindrical in a closed or collapsed position such that a cross section through the implant is at least partially circular, as shown in FIG. 2 with the shape of each element shown in FIG. 4. Implant 100 is comprised of biocompatible material, for example titanium or titanium alloy, and may be manufactured from a tubular body using lathe, laser, and/or electro-erosion manufacturing techniques. Alternatively, additive manufacturing techniques or cast manufacturing may be used.

Implant 100 includes a first end element 110 and a second end element 120, each being hollow and having a cylindrical shape with tapered portions as shown in FIGS. 2-5. In other examples, the exact shape of the end elements may vary from that shown. In the implementation shown in FIGS. 1-5, a leading, or distal, end of the implant near an anterior side 2 of vertebra 10 corresponds to the second end element 120 while a proximal end closest to a user inserting the implant into a bone near a posterior side 4 corresponds to the first end element 110. The end elements 110, 120 are intended to be brought towards one another to allow the expansion of the implant, as represented by a comparison of FIG. 2 with FIGS. 3 and 4, for example. Accordingly, the two end elements 110, 120 are connected to each other through interconnecting elements including a first group of upper arms 162, 163A-B and a second group of upper arms 172, 173A-B via a plate 130, and separately through interconnecting elements including a first pair of lower arms 152A-B and a second pair of lower arms 182A-B via a long blade 140. As seen in FIG. 2, each of these arms is rectilinear and in parallel with the other arms when implant 100 is in the closed, i.e., collapsed configuration. The configuration of the upper and the lower arms is such that space is provided therebetween in the collapsed position so that a retaining element or other actuation structure may fit inside the implant. Notably, a longitudinal axis of each arm 152A-B is offset from a longitudinal axis of each arm 182A-B, the offset denoted by reference numeral 149 in FIG. 2. In one example, the offset is 0.6 mm to ensure the long blade rotates away from longitudinal axis 102 during expansion of the implant. As referenced herein, longitudinal axis 102 is linear. Longitudinal axis 102 is also referred to herein as linear longitudinal axis. In other examples, the offset is an amount ranging from 0.5 mm to 0.7 mm.

As shown in FIG. 4, each of first end element 110 and second end element 120 includes an opening therethrough, 111 and 121, respectively. These openings 111, 121 are sized to accommodate the placement of a shaft of a tool therein, e.g., retaining element 103, the shaft being rotatable to control actuation of the implant. Further, an inner surface 116, 126 of the respective end elements 110, 120 may include ridges, threads or other engagement features to provide for controlled interaction between the tool and the implant. In one example, the first end element 110 or second end element 120 which is operational as a distal end of the implant may include a cavity with an enclosure on one side instead of a through opening so that the end element is entirely closed on an outward facing surface facing away from the remainder of the implant.

Figure 5:
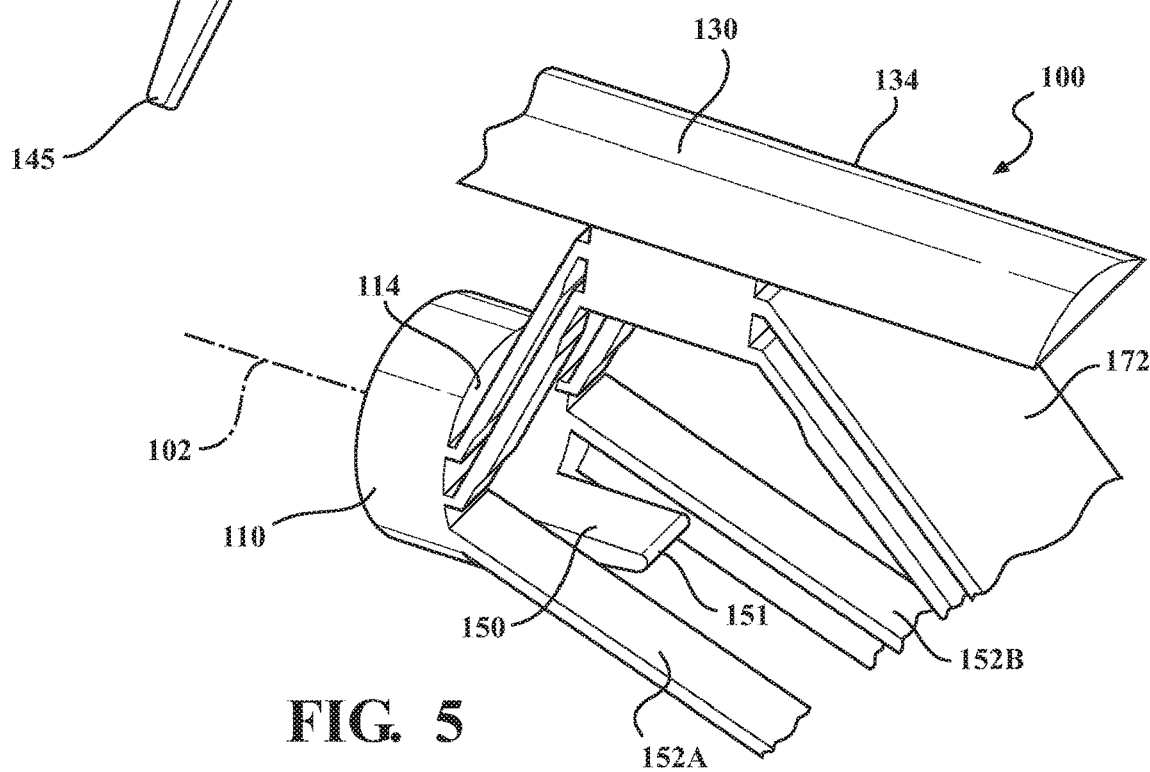
FIG. 5 is a close up perspective view of a portion of the implant of FIG. 1.

Continuing to refer to the end elements, first end element 110 includes a first inward facing surface 114 as shown, for example, in FIGS. 2-5. First inward facing surface 114 is ring shaped with opening 111 passing therethrough. Extending from first inward facing surface 114 are upper arms 163A-B, upper arm 162, lower arms 152A-B, and short blade 150. Taking plate 130 to be on an upper portion of implant 100 and long blade 140 to be on a lower portion, upper arm 162 extends from first inward facing surface 114 to plate 130 from a location on surface 114 above the other arms Immediately below upper arm 162 and also extending from surface 114 to plate 130 is a pair of upper arms 163A-B, as shown in FIG. 4. Upper arm 163A extends from a lateral side of surface 114 opposite that of upper arm 163B, as shown in FIG. 4. Extending from surface 114 below the upper arms to long blade 140 is a pair of lower arms 152A-B. In a manner similar to arms 163A-B, lower arm 152A extends from a lateral side of surface 114 opposite that of lower arm 152B. A space in between attachment locations of arms 152A and 152B, respectively, accommodates attachment of short blade 150 to end element 110. In this manner, short blade 150 extends from surface 114 in between lower arm 152A and lower arm 152B to a free end tip 151, as shown in FIGS. 2 and 5, for example. Short blade 150 includes a top surface in parallel with axis 102 and includes a tapering bottom surface 153 such that the short blade becomes smaller towards free end tip 151.

Second end element 120 includes a second inward facing surface 124 with arms 172, 173A-B and 182A-B extending therefrom in the same manner as described above for first end element 110. Thus, each of upper arms 172, 173A-B extend from second inward facing surface 124 to plate 130 while each of lower arms 182A-B extend from second inward facing surface 124 to long blade 140.

Plate 130 includes a convex upper surface 134 as shown in FIG. 4, curved in a direction transverse to axis 102. While implant is in a closed position, as shown in FIG. 2, plate 130 has a length close to a distance between first and second end elements 110, 120. In other variations, the length of the plate relative to the distance between the first and the second end elements may be greater or lesser than that shown in FIG. 2. In a central region of plate 130 and extending inward from a body of plate 130 toward axis 102 is a base portion 132. Base portion has a length extending over a central portion of the plate length between a first end surface 135 and a second end surface 136. Arms 162, 163A-B extend from first end surface 135 of base portion 132 while arms 172, 173A-B extend from second surface 136 of base portion 132, as best shown in FIGS. 3 and 5. Base portion 132 is one example of an attachment point between plate 130 and the upper arms.

As noted above, the upper arms include first group of upper arms 162, 163A-B and second group of upper arms 172, 173A-B. Having described where each arm interfaces with other structures of implant 100 at its ends, we turn to the structures of the arms themselves. Upper arms 162, 172 each have a width close to a diameter of the first and the second end elements. Upper arms 163A-B and 173A-B are pairs of arms below arms 162, 172, respectively, and are narrower than arms 162, 172. Each of the upper arms (and lower arms) has a thin web of material, also described as a material web, at its opposite ends. This material web undergoes plastic deformation when subject to loading, thereby functioning as an effective pivot point for adjacent elements. Put another way, through plastic deformation of the web material, an arm folds under the plate (or blade) as the first end element and the second end element are brought closer to one another, while the plate translates, or blade rotates, away from the central linear axis 102. Further, the material web is an articulation area formed by the thinning of a wall that is interposed between an end element and the plate or the blade. In one example, the material web is a weakened zone of material. In another example, the material web is formed through fabrication of a groove in the arm. Such a material web provides one example of a material web that is plastically deformable without breaking. In some examples, the material webs control the expansion of the implant by deforming in a predetermined manner to a predetermined extent. Further variations on the material web may be as described in U.S. Pat. No. 7,846,206 (the '206 Patent), U.S. Pat. No. 8,986,386 (the '386 Patent), and U.S. Pat. No. 9,414,933 (the '933 Patent), the disclosures of which are hereby incorporated by reference herein.

On the upper arms, arm 162 has webs 164, 166, and arms 163A-B have webs 167A-B, 168A-B. One end of each arm 162, 163A-B abuts first end element 110 while the other abuts surface 135 of base portion 132. Similarly, upper arms 172 and 173A-B opposite the aforementioned arms also include material webs at their ends abutting surface 124 of second end element 120 at one end and surface 136 of base portion 132 at an opposite end. In particular, material webs 174, 176, 177A-B and 178A-B correspond to material webs 164, 166, 167A-B and 168A-B, respectively.

Long blade 140 includes a base 142 attached to the remainder of implant 100 and has a length extending from base 142 to a free end tip 145, as shown in FIGS. 2-4. Tip 145 is a free end in that it is free of attachment to another element in the collapsed position, the expanded position, and at positions in between. Long blade 140 includes a central portion 141 and a tapered portion 144, the tapered portion terminating at free end tip 145. With tapered portion 144, long blade 140 has a tip that is sharpened to an extent. The geometry of long blade 140, particularly the tapered portion, improves its ability to bend when subject to loading. A lower surface of long blade, facing away from the remainder of implant 100, is defined by a ridge 146 having a peak aligned with a central axis of long blade 140 and extending along a length of blade 140, as best shown in FIG. 4. The length of blade 140 is such that free end tip 145 extends directly under short blade 150 when implant 100 is in a collapsed position, as shown in FIG. 2. In particular, tapered portion 144 of long blade 140 is positioned directly under tapered surface 153 of short blade 152 when the implant is in the collapsed position such that short blade 150 does not prevent long blade 140 from being positionable parallel to linear longitudinal axis 102. Nonetheless, free end tip 145 of long blade 140 is close to first inward facing surface 114 when implant 100 is in the collapsed position. As noted above, blade 140 is connected to the remainder of implant 100 via first pair of lower arms 152A-B extending from a first end 147 of base 142 and second pair of lower arms 182A-B extending from a second end 148 of base 142. Base 142 is one example of an attachment point between the long blade and the lower arms.

As seen in FIG. 2, base 142 is positioned closer to second end element 120 than first end element 110 such that arms 152A-B are much longer than arms 182A-B. The position of base 142 on the implant provides room for blade to extend across a significant portion of the implant length so that a longer blade is accommodated. As will be described in greater detail below, the longer blade is advantageous in that it allows for a larger sweeping motion below the implant to remove a greater volume of cancellous bone from the proximal end of the implant toward the distal end of the implant as the blade sweeps downward, as shown in FIG. 3, or alternatively, from the distal end to the proximal end, when the implant is structured with a blade oriented in an opposite direction.

Lower arms 152A-B include structure similar to that of the upper arms described above. Each lower arm 152A, 152B has a length extending from first end element 110 to long blade 140, a material web 154A-B abutting first end element 110 and a material web 156A-B abutting base 142 of long blade 140. As shown in FIGS. 4 and 5, a gap exists between arms 152A and 152B. Lower arms 182A-B include a material web adjoining second end 148 of base 142 to second end element 120. As shown in FIGS. 2 and 3, lower arms 182A-B have a constant thickness over their respective lengths, although it is contemplated that the specific sectional dimensions may vary over the arm length. In one example, the lower arms between base 142 and second end element 120 include a larger cross-sectional size further from their ends to cause plastic deformation to occur at a desired point on the arm, such as adjacent to the second end element. As shown in FIGS. 2-4, expansion of plate 130 and long blade 140 occur in a single plane. Thus, in the collapsed position shown in FIG. 2, in the expanded position shown in FIG. 3, and in positions in between, the plate, long blade, and arms of the implant are all in a single, common plane.

In one implementation, implant 200 is as shown in FIG. 6. In FIG. 6, like reference numerals refer to like elements, and unless otherwise indicated, referenced elements may be as described for implant 100, but within the 200-series of numbers Implant 200 includes a first end element 210, a first inward facing surface 214, a second end element 220, a second inward facing surface 224, a plate 230, and a long blade 240. Long blade 240 is attached to first end element 210 and second end element 220 via first pair of lower arms 252A-B and second pair of lower arms 282A-B, respectively. The first pair of lower arms 252A-B extending from a first end 247 of base 242 and the second pair of lower arms 282A-B extending from a second end 248 of base 142. Lower arms 252A-B include material web 254A-B at an end abutting first end element 210 while at an opposite end, arm 252A-B forms one part of a ball and socket joint. As shown in FIG. 6, each of arms 252A-B provide the ball component while the first end 247 of base 242 of blade 240 provides sockets (not shown) corresponding to the ball components. In this manner, a surface at the first end 247 of base 242 includes recessed surfaces (not shown) to receive the ends of arms 252A-B. In an alternative configuration, the elements are reversed such that the arms 252A-B have a socket on their end surfaces and base 242 has protrusions to define the ball of the ball and socket. The ball and socket is designed so that long blade 240 and arms 252A-B pivot about the ball and socket connection, while the connection point rotates away from linear axis 202. This rotational movement minors that occurring during expansion of implant 100 that includes material web 156A-B, such as is shown in FIGS. 2-3. As such, the ball and socket connection provides for the relative movement of elements as described in implementations having a material web connection between the lower arm and the long blade while also preserving the attachment between lower arms 252A-B and long blade 240 during expansion. Additionally, in this arrangement arms still undergo one way expansion via plastic deformation of material webs 254A-B and 282A-B, for example. It should be appreciated that functional equivalents of a ball and socket joint may also be used in place of the ball and socket of this implementation.

In one implementation, an implant 300 includes lower arms 352A-B attached to long blade 340 through a frangible material segment 356A as shown in FIG. 7. Frangible material segment 356A provides the only connection between each lower arm 352A-B and long blade 340, and it can be seen in FIG. 7 that an end face of arms 352A-B is not attached to first end 347 of base 342. Frangible material segment 356A provides a support function so that prior to use of the implant, when the implant is closed and in the collapsed position, blade 340 is held in position in part through support by the arms 352A-B via frangible material segment 356A, as shown in FIG. 7. However, implant 300 is structured so that when load is applied to the first end element, i.e., when the first end element of the implant moves closer to the second end element, and the plate and blade are subject to loads causing them to move further apart and expand, movement of arms 352A-B and long blade 340 causes tension therebetween such that frangible material segment 356A breaks. In this manner, implant 300 is structured so that long blade 340 is pivotable about the lower arm located between base 342 and the second end element upon breakage of frangible material segment 356A.

In FIG. 8, another implementation of the implant is shown where like reference numerals refer to like elements, within the 400-series of numbers Implant 400 includes a first end element 410, a second end element 420, a plate 430, a base 432, a group of upper arms 462, 463A-B, 472, 473A-B, a long blade 440, and a group of lower arms 452A-B, 482A-B. Lower arms 452A-B, 482A-B and blades 440, 450, however, are reversed relative to the end elements of implant 100. In particular, base 442 of long blade 440 is adjacent to first end 410 of implant 100. In this manner, implant 400 is configured so that when first end element is moving closer to second end element during expansion of the implant, free end tip 445 of long blade 440 arcs away from central axis 402. This arcuate motion is downward and away from second end element 420 and in a proximal direction toward the user. Thus, when implant 400 is inserted into a vertebra, for example, long blade 440 is attached so that it expands in an arcuate manner from an anterior side toward a posterior side of the vertebra.

Figure 9:
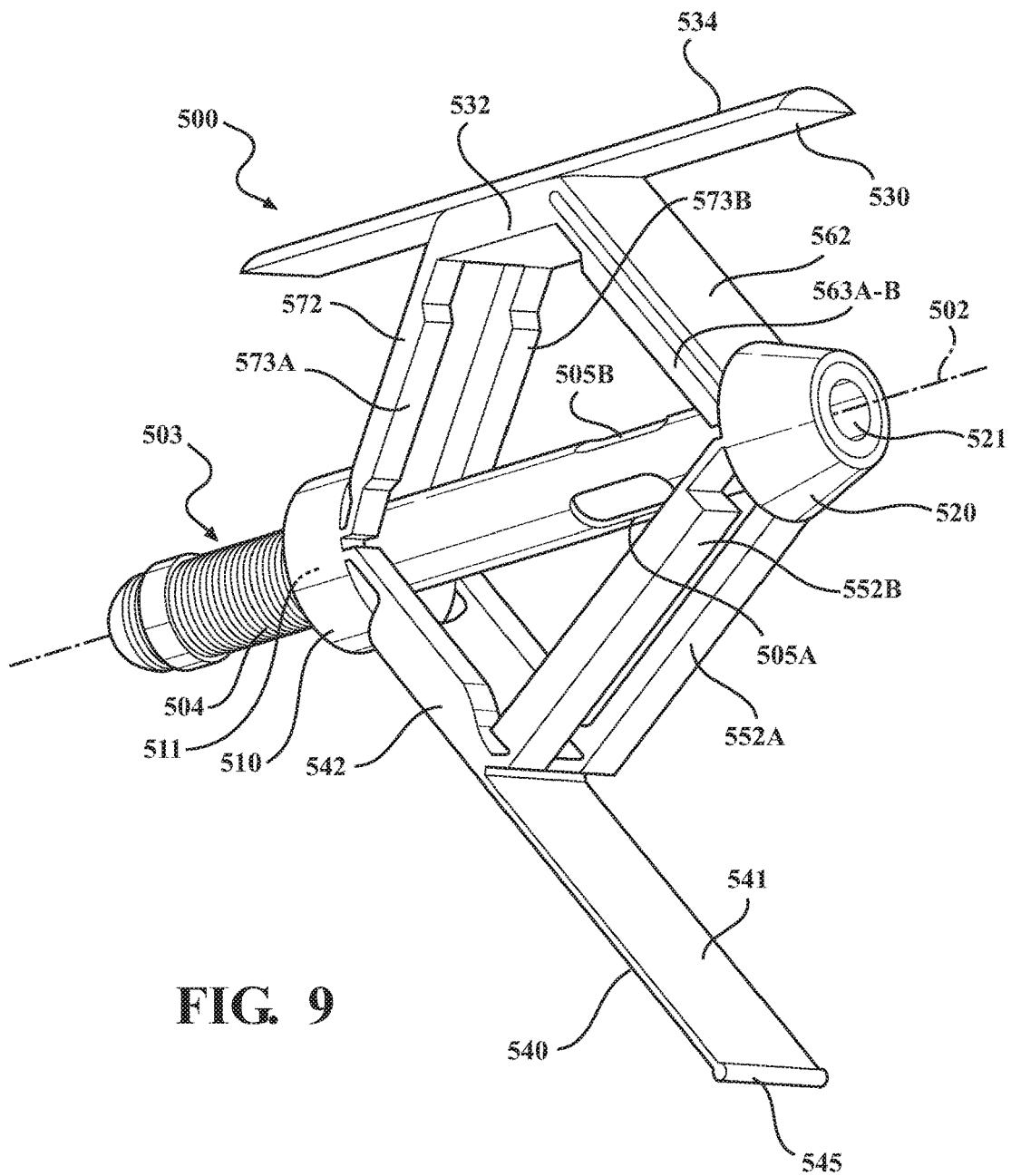
FIG. 9 is a perspective view of an implant according to one implementation of the disclosure.

In FIGS. 9-11, another implementation of the implant is shown where like reference numerals refer to like elements, within the 500-series of numbers Implant 500 includes a first end element 510, a second end element 520, a plate 530, a base 532, a group of upper arms 562, 563A-B, 572, 573A-B, a long blade 540, and a group of lower arms 552A-B, 582A-B. As shown in FIG. 9, each of first end element 510 and second end element 520 includes an opening therethrough, 511 and 521, respectively. These openings 511, 521 are sized to accommodate the placement of a shaft of a tool therein, e.g., retaining element 503 with ridged portion 504, the shaft being rotatable to control actuation of the implant. Retaining element 503 includes egress apertures 505A, 505B, through which cement 30 exits retaining element 503 and enters the cavity within the bone.

FIG. 10, shows that arms 582A-B, effectively material webs, connecting blade 540 to first end element 510, are thicker than corresponding material webs 564, 567A-B of the upper arms. Because there is only one arm layer on the lower side of the implant, the material web is thicker to compensate for the single level of support and to provide sufficient capacity to transfer loads. In one example, arms 582A-B are 0.4 mm thick. Additionally, as shown by reference numeral 549 in FIG. 10, a longitudinal axis through arms 582A-B is offset from a longitudinal axis through arms 552A-B such that arms 552A-B are further from linear longitudinal axis 502. The arms are offset by an amount to optimize the expansion function of the blade, i.e., to ensure the blade expands outwardly when first end element and second end element move toward one another. In one example, the offset is 0.6 mm. In other examples, the offset is an amount ranging from 0.5 mm to 0.7 mm Inclusion of arms offset 549 from one another on the lower side of the implant is rendered simpler due to the additional space available with only a single layer of arms on the lower side of implant 500, as shown in FIG. 10.

On the upper arms, upper arm 562 has webs 564, 566, and arms 563A-B have webs 567A-B, 568A-B. One end of each arm 562, 563A-B abuts abutting surface 524 of second end element 520 while the other abuts surface 535 of base portion 532. Similarly, upper arms 572 and 573A-B opposite the aforementioned arms also include material webs at their ends abutting first end element 510 at one end and surface 536 of base portion 532 at an opposite end. In particular, material webs 574, 576, 577A-B and 578A-B correspond to material webs 564, 566, 567A-B and 568A-B, respectively.

As shown in FIGS. 9-11, blade 540 is flat on an upward facing side 541 and wider relative to an outer width of the implant compared to long blade 140. In particular, FIG. 11 illustrates that a width of long blade 540 through tapered portions 543, 544 is only slightly narrower than base 542, where base 542 has a width corresponding to an outer width of implant 500. Blade 540 includes a first tapered portion 543 extending from base 542 and a second tapered portion 544 extending from first tapered portion 543 to tip 545. Each tapered portion is defined by a planar surface, as shown in FIG. 11, becoming wider toward tip 545. Bottom surfaces 546 outside the planar tapered portions 543, 544 may be slightly curved or rounded, again, shown in FIG. 11. The geometry of blade 540, and in particular, its downward facing surface area, shown in FIG. 11, for example, is maximized relative to the outer dimensions of the implant. Put another way, a length of the blade is close to a length of the implant while a width of the blade is close to a width of the implant. This geometry maximizes the capacity of the blade to displace material, such as cancellous bone, as the implant is expanded. Tip 545 is rounded or bulbous, and extends across the width of long blade 540. In one example, an angle of taper for first tapered portion is two degrees and for second tapered portion is four degrees. In this example, providing a second tapered portion 6 to 7 mm in length further optimizes the ability of the long blade to bend when subject to a predetermined load. A second tapered portion 6.7 mm in length is particularly advantageous. In this and other examples, the sectional radius of rounded tip may be 0.30 mm. In one example, the long blade is 4.1 mm in width while the widest location on the planar surface of the second tapered portion adjacent to the tip is 3.6 mm.

Base 542 of long blade 540 is adjacent to first end element 110 so that free end tip 545 of long blade 540 arcs away from second end element 120 and toward first end, i.e., in a proximal direction. In an alternative configuration, the base may be positioned in a reverse configuration and adjacent to the second end element 120 so that tip 545 of long blade 540 arcs away from linear longitudinal axis 502 in an opposite direction from that exhibited by implant 500 shown in FIG. 9.

As discussed above, one advantage of implant 500 when inserted and expanded in a bone structure, such as a vertebra, is that it includes a blade with a large surface area, so that during an expansion process when the blade arcs away from linear longitudinal axis 502, a volume of cancellous bone is displaced that corresponds to the width of the blade, the large relative width of the blade increasing the volume displaced. In turn, the increased displacement of cancellous bone creates a wider cavity below the implant so that a greater amount of cement can be disposed therein to complete a repair using the implant. Additionally, in instances where the blade path causes the tip of the blade to contact a lower plate, the geometry of the blade is such that the blade bends and otherwise deforms when subject to loading, due to contact with a cortical bone surface, for example, thereby reducing the possibility that tip 545 of blade will puncture the vertebral body when load continues to be applied to blade after it makes contact with the cortical bone. This advantage is further enhanced because tip 545 of blade 540 is rounded, as shown in FIGS. 9 and 10, for example, reducing the risk of cortical bone puncture.

Figure 12:
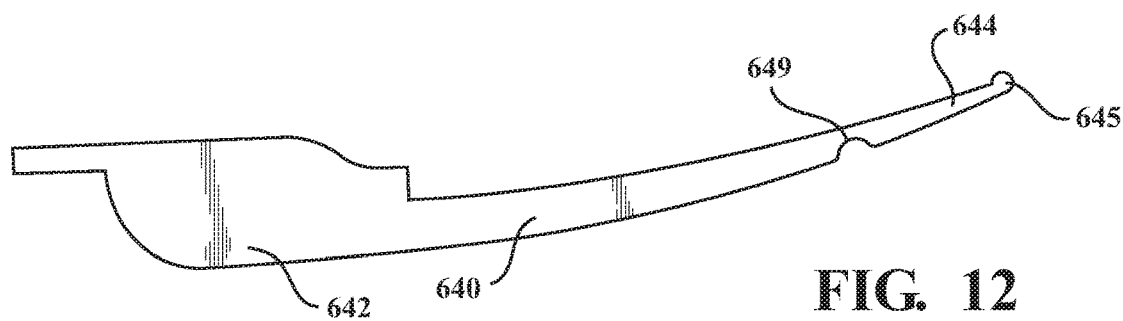
FIG. 12 is a side view of a blade of an implant according to one implementation of the disclosure.

In another implementation, the implant of FIGS. 9-11 includes a blade 640 as shown in FIG. 12. This blade includes base 642, and a weak section in the form of recess 649 across the blade width defining a weak point in the blade structure. In other respects, like reference numerals refer to like elements in implant 500. Blade 640 is advantageous in that when blade 640 is under load and in contact with a cortical bone, a distal portion 644 of blade 640 between recess 649 and free end 645 will bend or break from the remainder of the blade and, irrespective of whether distal portion 644 bends or breaks, blade 640 will not penetrate the bone. This provides an added measure of protection to ensure no cortical bone is punctured when the implant is inserted into and expanded within a vertebral body. In other examples, a feature similar to recess 649 may be employed in a blade of any implant implementation described herein.

Figure 13:
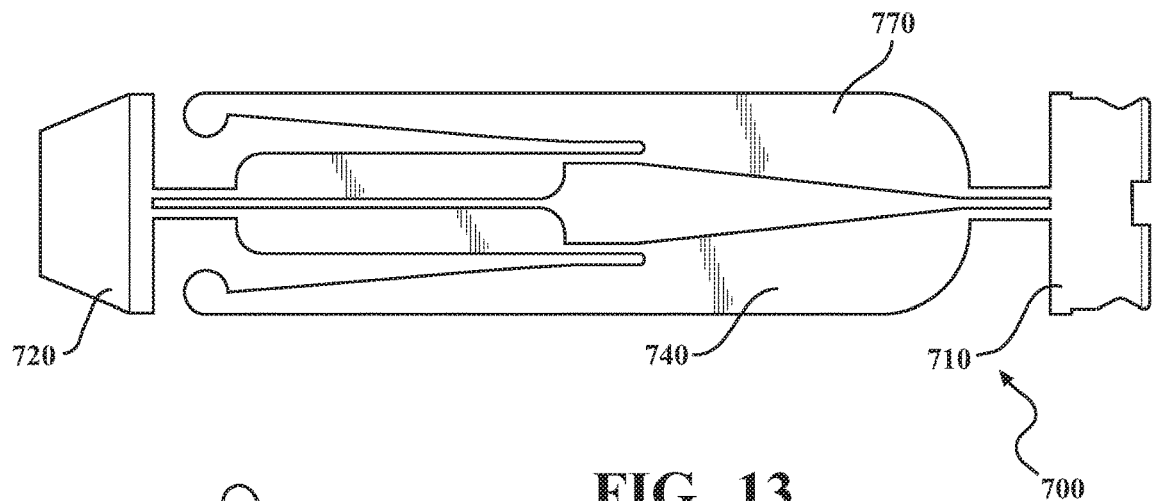
FIGS. 13 and 14 are side views of an implant in different positions according to one implementation of the disclosure.
Figure 14:
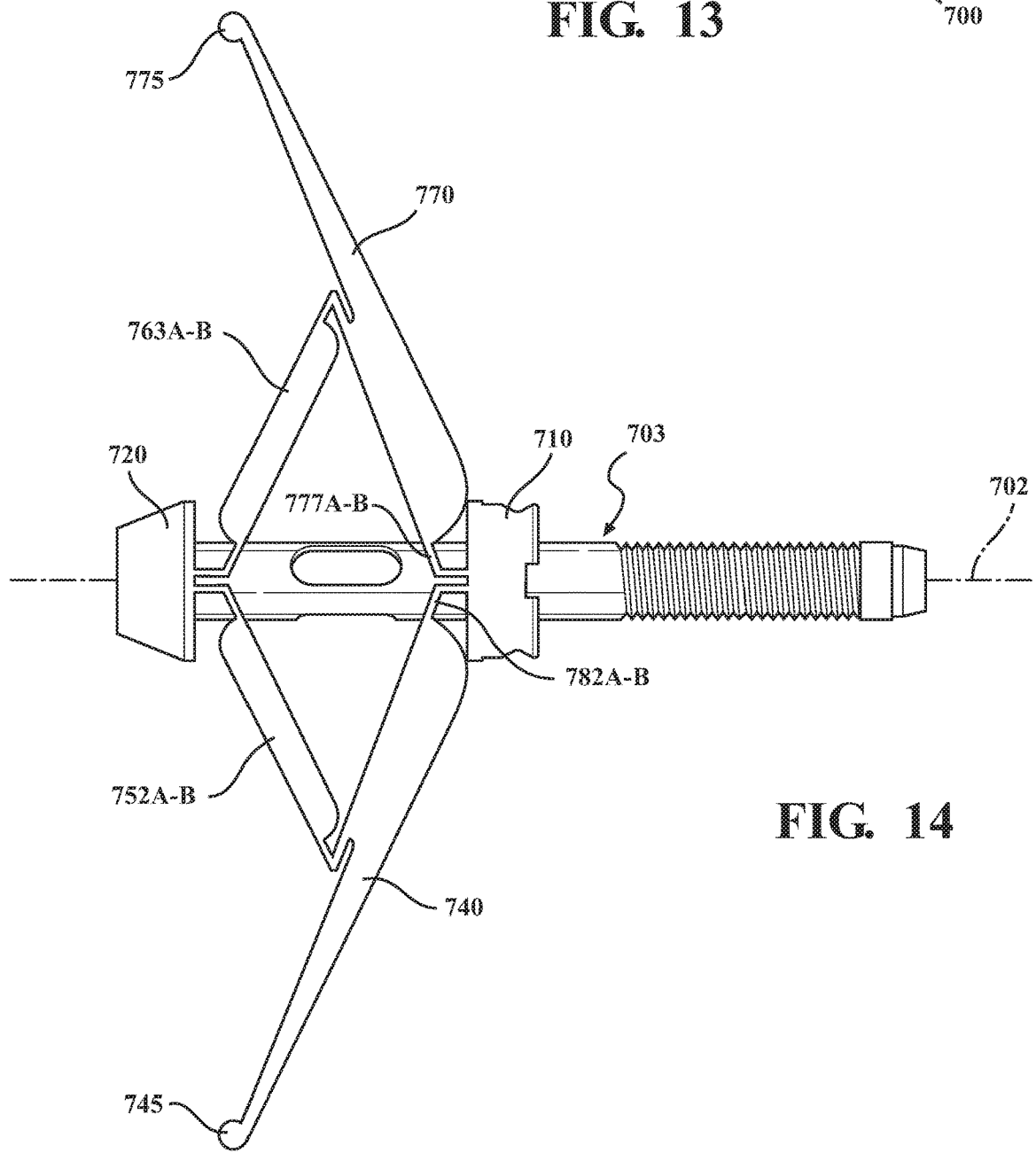

In yet another implementation, an implant 700 includes two blades: an upper blade 770 and a lower blade 740, as shown in FIGS. 13 and 14. Unless otherwise noted, like reference numerals refer to like elements. Below linear longitudinal axis 702 is lower blade 740 and above linear longitudinal axis 702 is upper blade 770. Arms 782A-B connect the lower blade 740 to first end element 710, and arms 752A-B connect the lower blade 740 to the second end element 720. Likewise, arms 777A-B connect the upper blade 770 to first end element 710, and arms 763A-B connect the upper blade 770 to the second end element 720. The arms 752A-B, 763A-B, 777A-B, 782A-B may be similar or the same as those in implant 500, for example. Implant 700 is symmetrical, and accordingly, features of upper arms and blade 770 are the same as those for lower arms and blade 740. FIG. 13 illustrates implant 700 in a collapsed position while FIG. 14 illustrates implant 700 in an expanded position.

The implant structure may be varied in many ways. For example, upper arms connecting an end element with the plate may be arranged so that a single arm connects the first end element to the plate and a single arm connects the second end element to the plate. To accommodate this structure, the web of each arm may have a greater thickness than in other implementations so that each arm can bear greater loads. In other configurations, the arms may be offset to a greater extent relative to a central longitudinal axis of the implant to provide space for a retaining element. An increased offset may be desirable where the arms are of larger cross-sectional size. Similar variations are possible in the lower arms. In another example, an implant includes a plate above a central longitudinal axis and two blades adjacent to one another below the central longitudinal axis. In this configuration, the two blades expand in a matching arcuate movement when the first and second end elements of the implant move toward one another. In other examples, a long blade of the implant may include a hinge in place of a recess so that a free end portion of the blade rotates upon contact with a cortical bone to prevent puncture during expansion of the blade. In yet another example, the tip may include a spring feature to serve a similar function. In other examples, the blades of the various implementations described herein may include rounding features at a tip of the blade to minimize the risk of cortical bone puncture during use. In still further examples, a cross-sectional shape of the plate, short or long blade, arms and end elements may vary from that shown in the depicted implementations. In other examples, the position of the long blade relative to the implant ends may be reversed relative the orientation described for each of the above implementations. Thus, if the long blade moves in an accurate manner from the anterior side of the vertebra toward the posterior side, it may also be structured to rotate from the posterior side to the anterior side.

In another aspect, the present disclosure relates to systems for repairing vertebral bodies. In one implementation, a system includes implant 100 and retaining element 103 attached thereto via placement of retaining element 103 into first and second end elements 110, 120 of implant 100, respectively. One example of such a system is shown in FIG.

1. Retaining element 103 provides a structure upon which end elements 110, 120 may be brought closer together through plastic deformation of the arms, e.g., material webs on the arms, while ensuring that implant 100 does not collapse after expansion.

In another implementation, a system may include an implant, a retaining element and an implant expander. In such an implementation, the implant expander is placed over the retaining element and contacts the implant during use when actuating the system to expand the implant. In yet another implementation, a system may include an implant, a retaining element, an implant expander and an injector transfer tube. With a fully expanded implant, the injector transfer tube is advanced and positioned within the implant expander. The injector transfer tube is configured so that cement filler may be injected from within the injector transfer tube into the bone structure repaired by the implant.

In another aspect, the implant may be included together with other tools as a kit. In one implementation, a kit includes two implants, and one or more of an implant expander, a trocar, a guidewire, a reamer, a template, a cannula plug and an injector transfer tube. In a variant, a plurality of any one of the aforementioned tools may be included. In a further variant, the kit includes a single implant along with a combination of the aforementioned tools. In yet another variant, the kit includes three or more implants. If the kit includes more than a single implant, the implants within the kit may vary in overall size or materials, from which the most suitable implant may be chosen for a particular surgery. Any combination of implants and tools may also be included in a single package or in separate packages which may be later brought together as a kit.

The kit may be varied in many ways. For example, it is contemplated that any combination of particular implants and tools as described herein may further include other tools or instruments not otherwise described as part of a kit. The various combinations of elements of any contemplated kit may be included in a single package or distributed among multiple packages. In other examples, the kits contemplated herein may be accompanied by an instruction manual on how to perform one or more of the methods of using the contents of the kit.

Figure 15:
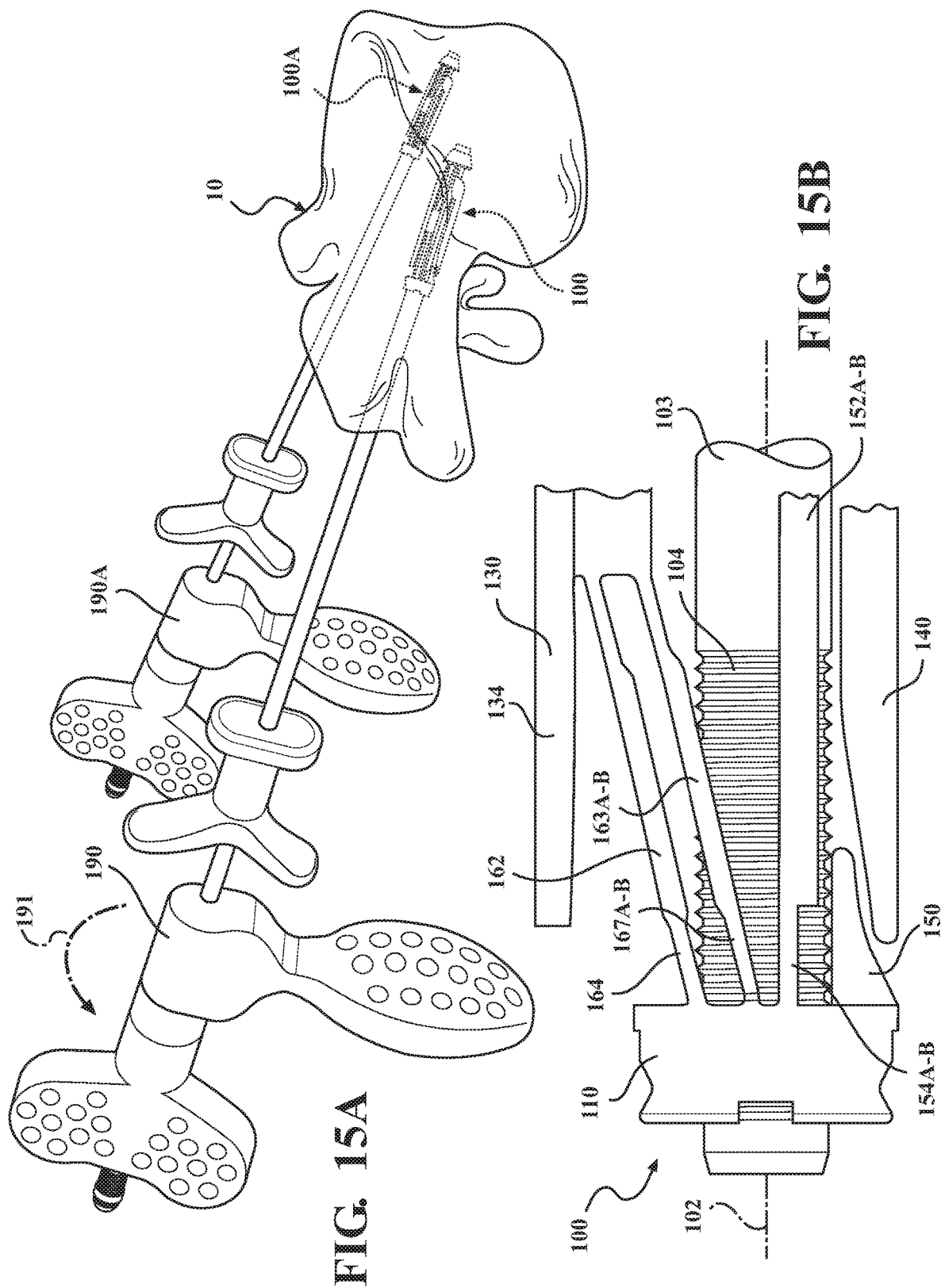
FIGS. 15A, 15B and 16-18 depict various steps of a method of inserting and expanding the implant in a bone according to one implementation of the disclosure.

In another aspect, the present disclosure relates to a method of using an implant to repair a collapsed bone structure. One implementation of this method is depicted in FIGS. 15A, 15B and 16-18. Initially, implant 100 is inserted into a collapsed bone structure such as a vertebral body, for example. This may be accomplished with the use of tools such as an implant expander 190 shown in FIG. 15A. To use the implant expander, the implant is attached to a distal end of the implant expander. In one example, this may be accomplished through threaded engagement between a rod (not shown) extending through a tube of the implant expander and an interior surface within second end element 120 of the implant. When the implant is attached, the tube of the implant expander that surrounds the rod abuts first end element 110. The tube is sized to pass over an exposed portion of retainer element 103. When the implant is first inserted, it is in a collapsed position, as shown in FIGS. 15A-15B. In some examples, the steps preceding insertion of the implant for the preparation of a portal into the vertebral body may be as described in the '206, '386 and '933 Patents. In another example, preparation involves the insertion of a trocar into the bone, followed by placement of a guidewire through the trocar. A portion of the trocar is then removed so that a reamer may be slid over the guidewire. This is followed by drilling into the bone and cleaning the drilled pathway. Other tools may also be used at this juncture, such as a cannula plug to verify the dimensions of the portal for implant placement. In the implementation shown in FIG. 15A, two portals in vertebra 10 are prepared for two implants 100, 100A, respectively. Nonetheless, it is contemplated that a repair may involve the placement of a single implant or multiple implants into the bone, a quantity of implants inserted chosen based on the severity of the deterioration or injury, and/or the size of the bone, for example.

With implant 100 in a desired position within the vertebral body, implant expander 190, and 190A if two portals in vertebra 10 are prepared for two implants 100 and 100A, is actuated by rotating a handle on the implant expander, denoted by 191 in FIG. 15A. Rotation of the handle causes the rod within the implant expander to translate axially toward the handle while simultaneously first end element 110 becomes closer to second end element 120. One example of a handle that provides such function includes an internal structure that converts the rotational actuation into a linear translation. During this process, the tube abutting first element 110 translates the same amount but in an opposite direction to translation of the second end element. Turning to FIG. 15B, retaining element 103 includes a ridged portion 104 so that as first end element 110 becomes closer to second end element 120, inner surface 116 defining opening 111 through first end element 110 is incrementally engageable with corresponding ridges 104 on retaining element 103. This is one feature that prevents implant 100 from returning to the collapsed position after expansion.

Figure 16:
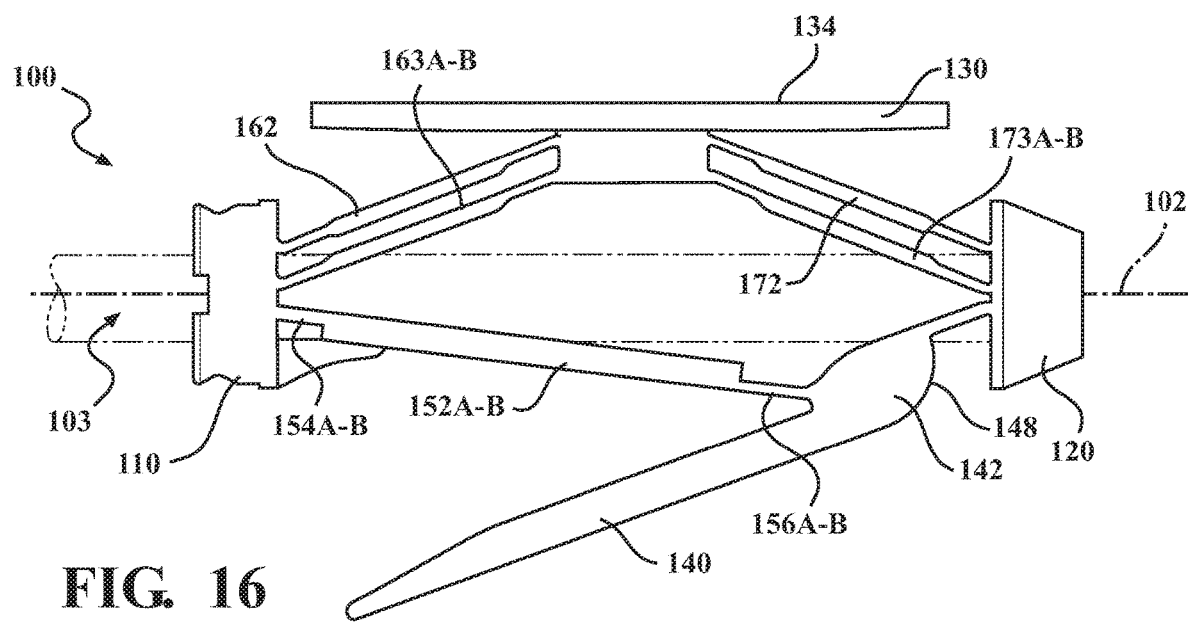

When first end element 110 moves toward second end element 120, each of the arms of implant 100 pivot about the end elements to which the arms are attached. In particular, and as shown in FIG. 16, arms 162, 163A-B pivot upward about their respective webs 164, 167A-B, along with a similar pivoting motion in the other upper arms 172, 173A-B. As the arms pivot, plate 130 translates upward in a plane through the implant while a length of plate 130 measured on bearing surface 134 remains parallel to linear longitudinal axis 102 (compare FIGS. 15B and 16). It should be appreciated that the orientation of the plate and the linear longitudinal axis may be substantially parallel, and that the plate may be oriented at a slight angle relative to the longitudinal axis due to surgical conditions or tolerances in the manufactured implant. As the plate translates in an upward direction, cancellous, i.e., soft bone within the vertebra is displaced by the plate. On the lower side of the implant, movement of end elements 110 and 120 toward one another cause arms 152A-B to pivot about material webs 154A-B, 156A-B and arms 182A-B to plastically deform, arms 182A-B functioning as material webs. This, in turn, causes long blade 140 to move in an arcuate manner about arms 182A-B, the arcuate movement being in the plane through the implant and in a downward direction. As with the expansion of the plate, arcuate movement of long blade 140 causes cancellous bone to be displaced in its path. Because of the length of long blade 140 and its path through the cancellous bone as it pivots about arms 182A-B, significantly more cancellous bone is displaced by long blade 140 compared with the upper plate 130. This is clear from FIG. 17, where a path of the blade on the lower side of the implant extends to a lower plate 12 of vertebral body 10 while a path of the plate on the upper side extends to the much closer upper plate 14 of vertebral body 10. The sharpened shape of long blade 140 through tapered portion 144 toward tip 145, best shown in FIG. 4, promotes cutting through the cancellous bone while the blade is rotated to reduce resistance during the expansion process. As noted above, deformation in the material webs that facilitates the pivoting action of the arms is plastic deformation, and accordingly, the plate and blade will remain in an expanded position following expansion.

During the expansion procedure, long blade 140 rotates due to base 142 being closer to second end element 120 than it is to first end element 110 and arms 152A-B being longer than arms 182A-B, as shown in FIG. 16. Rotation is also facilitated due to offset 149 between arms 152A-B and arms 182A-B. Thus, as the lower arms pivot, base 142 rotates counterclockwise, causing tip 145 of long blade 140 to travel in an arc from its starting position shown in FIG. 15B toward anterior side 2 and bottom plate 12 of vertebra 10 (shown in a later procedural step in FIG. 18). As an added measure to ensure long blade 140 travels downward, short blade 150 is positioned to prevent long blade 140 from rotating toward a central region of the implant. In its starting position, long blade 140 is parallel to linear longitudinal axis 102, as shown in part in FIG. 15B. During expansion, long blade 140 becomes angled relative to linear longitudinal axis 102 and moves further away from linear longitudinal axis 102 as end portions 110, 120 are moved toward one another. Because arms 152A-B are positioned on lateral sides of short blade 150, each arm 152A-B pivots past short blade 150 without interference.

Figure 17:
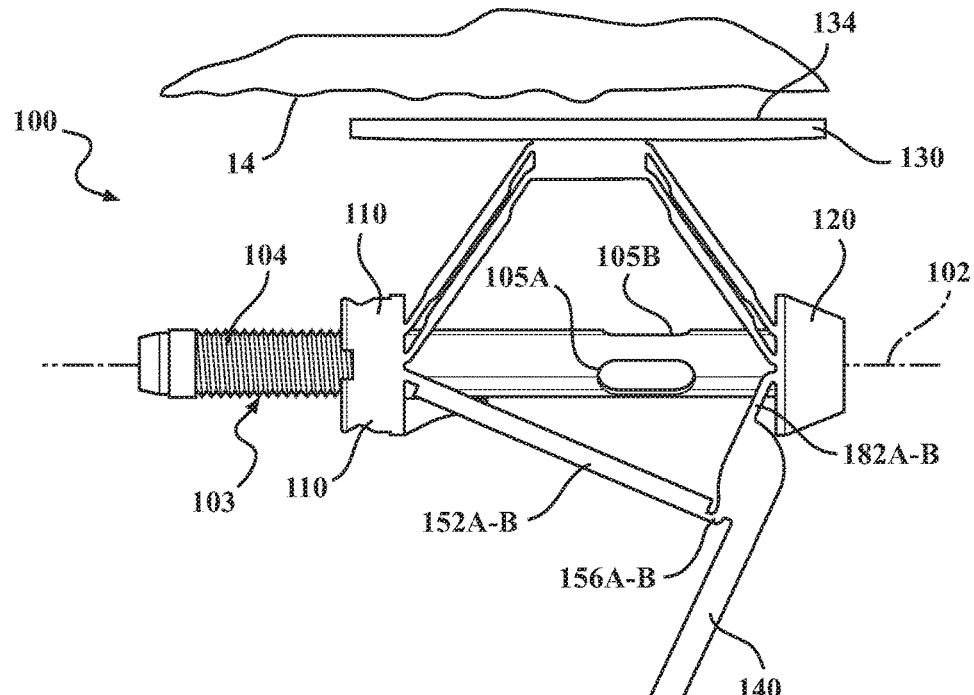

FIG. 16 shows implant 100 partially expanded. Once implant 100 is fully actuated, it is positioned as shown in FIG. 17. One advantage of implant 100 is that through its expansion, plate 130 operates to restore the depth, i.e., height, of the vertebral body above the implant. Another advantage of bone restoration using implant 100 is that, when expanded, it creates a path for cement in the bone that traverses nearly the entire depth of the vertebral body through the expansion of plate 130 and blade 140. In particular, and as is shown in FIG. 17, this is accomplished through the formation of a cavity extending between surface 134 of plate 130 abutting an interior cortical surface of top plate 14 and tip 145 of blade 140 abutting an interior cortical surface of bottom plate 12. As will be described further below, the creation of a cavity extending between plates 12 and 14 provides room for cement to be deposited throughout a depth of the vertebral body thereby creating a more durable repair than one where cement only fills a portion of the bone depth. Additionally, in variants where the plate and/or the blade have a width close to that of the implant, compared to variants with plates and/or blades having a narrower width, a volume of cancellous bone displaced is maximized, further increasing the amount of cement that can be disposed in the bone cavity for the repair and improving the distribution of cement in the cavity. Thus, implant 100 is used to create a cavity so that sufficient cement is deposited throughout the bone depth to minimize any loss of restored bone height following surgery.

Although long blade 140 is shown expanded at a particular angle in FIG. 17, the angle for full expansion may be varied as a matter of design choice to suit surgical needs. For example, an angle between linear longitudinal axis 102 and long blade 140 in the expanded position may be thirty degrees, sixty degrees or eighty degrees. In one example, as the implant is expanded toward the expanded position, the plate expands a first distance from the linear longitudinal axis and the tip of the blade expands a second distance from the linear longitudinal axis in a manner such that a difference between the second distance and the first distance becomes greater as the implant becomes closer to reaching the expanded position. In some examples, a distance from the linear longitudinal axis of the implant to the tip of the blade is nearly three times a distance measured from the linear longitudinal axis to the plate when the implant is fully expanded.

Figure 18:
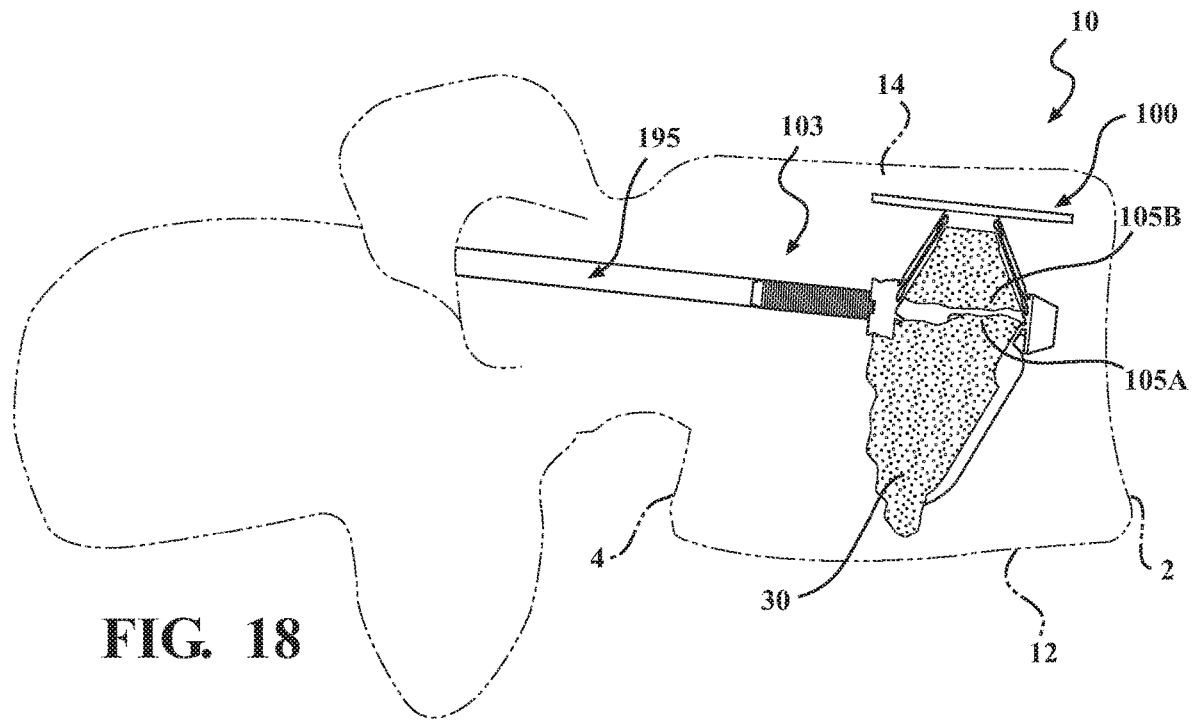

Once implant 100 is properly positioned and fully expanded, an injector transfer tube 195 is inserted over retaining element 103 and cement 30, e.g., bone cement, is injected through the transfer tube and into a space within the vertebra previously cleared of cancellous bone, as described above. Retaining element 103 includes egress apertures 105A, 105B, through which cement 30 exits retaining element 103 and enters the cavity within the bone, as shown in FIG. 18. This form of cement injection is also described in at least some implementations of the '206, '386 and '933 Patents, along with other alternatives and variations. As cement 30 is injected into the cavity through the egress apertures 105A, 105B, it flows at least in part through the gap between arms 152A and 152B. Thus, the gap between arms 152A, 152B provides improved flow of cement into the cavity, thereby improving the overall structural repair. Because the cavity formed in the vertebra extends close to respective plates 12 and 14, i.e., cortical bone endplates, the cement fills nearly the entire, or in some cases the entire depth of the vertebra. The cement thereby fulfills a load bearing function between plates 12 and 14 once the cavity is filled. Put another way, since the cement is disposed through the depth of the vertebral body, it functions to prevent the bone from collapsing over time, as there is little to no bone depth without support provided by the cement. Further, even where implant 100 does not have plate to plate contact as shown, the plate and blade are each close enough to the cortical bone surfaces in the expanded position so that cement injected into the bone ensures that recompression of the bone is prevented or minimized following the restoration procedure. In some examples, a second implant, such as implant 100A shown in FIG. 15A, may be expanded in conjunction with and simultaneous to the expansion of implant 100. The steps for expanding implant 100A from a collapsed position to an expanded position are the same as those for implant 100.

Figure 19:
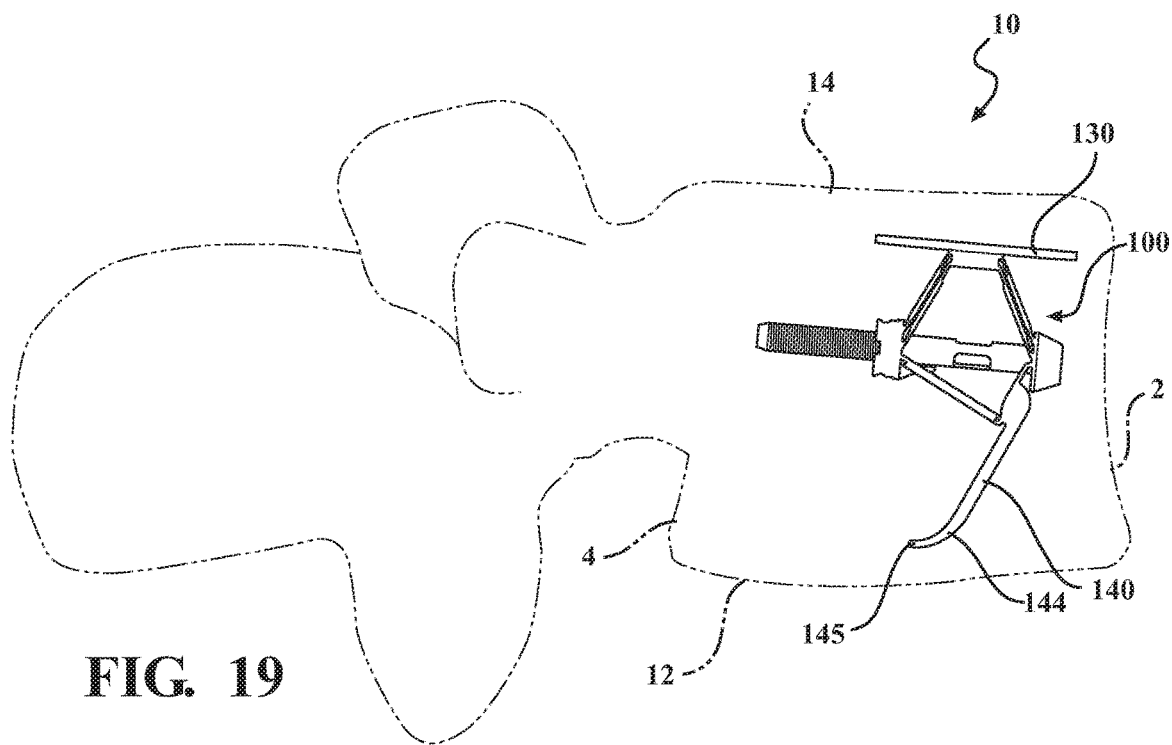
FIG. 19 depicts a step in a method of placing an implant into a bone according to one implementation of the disclosure.

In another implementation of the method, blade 140 is longer than a distance from linear longitudinal axis 102 of implant 100 to a bottom plate 12 of the vertebra. This circumstance may occur due to the size of the bone designated for repair or due to the placement location of the implant. In this instance, once the expansion of the implant proceeds so that tip 145 of blade 140 approaches bottom plate 12, the blade begins to bend inwardly over bottom plate 12, as shown in FIG. 19. As shown in FIG. 3 and described above, blade 140 includes a tapered portion 144 toward tip 145 shaped so that a free end of blade 140 may bend when subject to a predetermined load. In some examples, the predetermined load will be determined based on an expected resistive force in a cortical bone surface to determine a load under which tapered portion 144 will yield. As shown in FIG. 19, bending of tapered portion 144 prevents blade 140 from penetrating bottom plate 12.

The preceding methods may also be performed using the implants shown in FIGS. 6-8 and described above. It is noted that operation of the implants of such implementations is substantially similar to that of implant 100.

Figure 20:
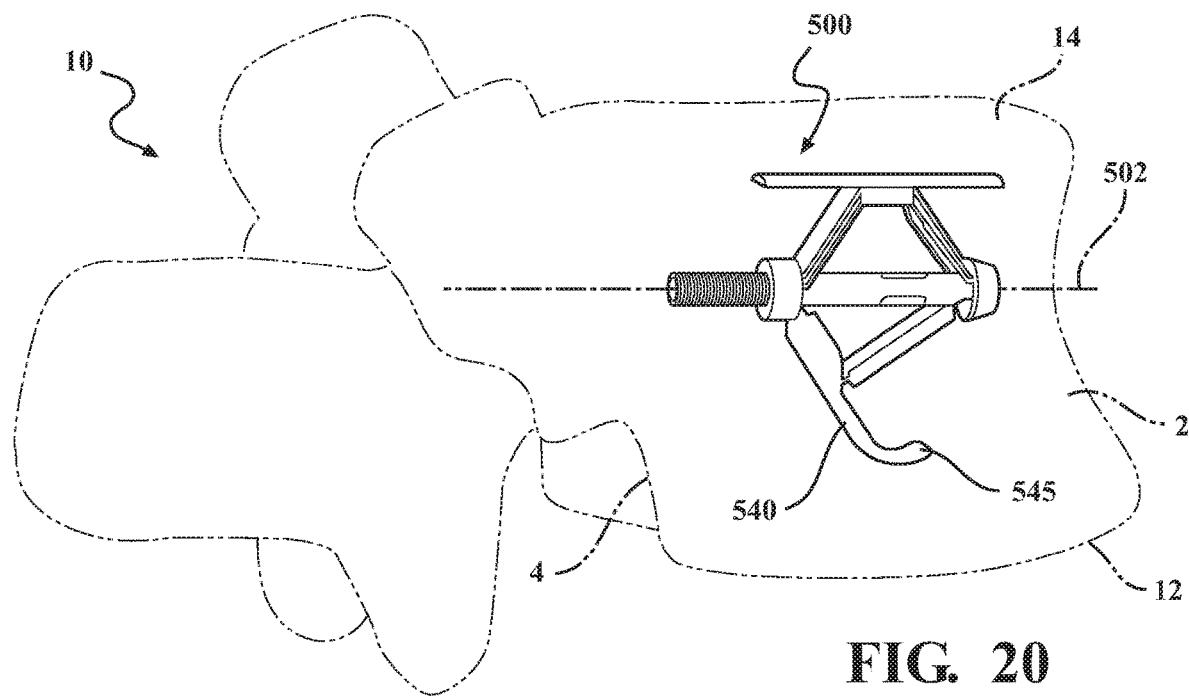
FIG. 20 depicts a step in a method of placing an implant into a bone according to one implementation of the disclosure.

In a variant of the above method, the same methodology is employed with implant 500. Although operatively similar to implant 100, blade 540 expands in an arc opposite that of blade 140, and tip 545 of blade 540 moves in an arcuate manner away from central axis 502 toward posterior side 4 of vertebra 10 during expansion, as shown in FIG. 20. Due to the width and the length of the blade being close to that of the overall implant, a volume of cancellous bone below the implant displaced by the blade during expansion of the implant is maximized using implant 500. This provides a path for the cement that is as large as possible based on the implant size, thereby creating improved conditions for the flow of cement into the cavity. Because the blade rotates about an axis toward one side of the implant, the tip of the blade extends further from the longitudinal axis of the implant than it would if positioned at a more central location on the implant. Through this structure, a cavity formed in a vertebral body extends not only to an upper plate, but also close to a lower plate via expansion of the blade. During injection of cement into a cavity formed by implant 500, cement flows, at least in part, through a gap between arms 552A and 552B, similarly to the cement flow path described for implant 100. The method steps are otherwise common to those described for the implementations above.

In some variants, when blade 540 is longer than the space available in vertebra 10 between implant 500 and bottom plate 12, blade 540 bends in a region of its tip 545, as shown in FIG. 20. In such instances, the tapering shape of the blade, best shown in FIG. 10, and the rounded, or bulbous tip are conductive to bending when subject to loads and advanced into contact with a cortical bone surface. Further, inclusion of a blade with a recess such as that shown in FIG. 12 also promotes bending of the blade, and does so at a predetermined location on the blade.

Figure 21:
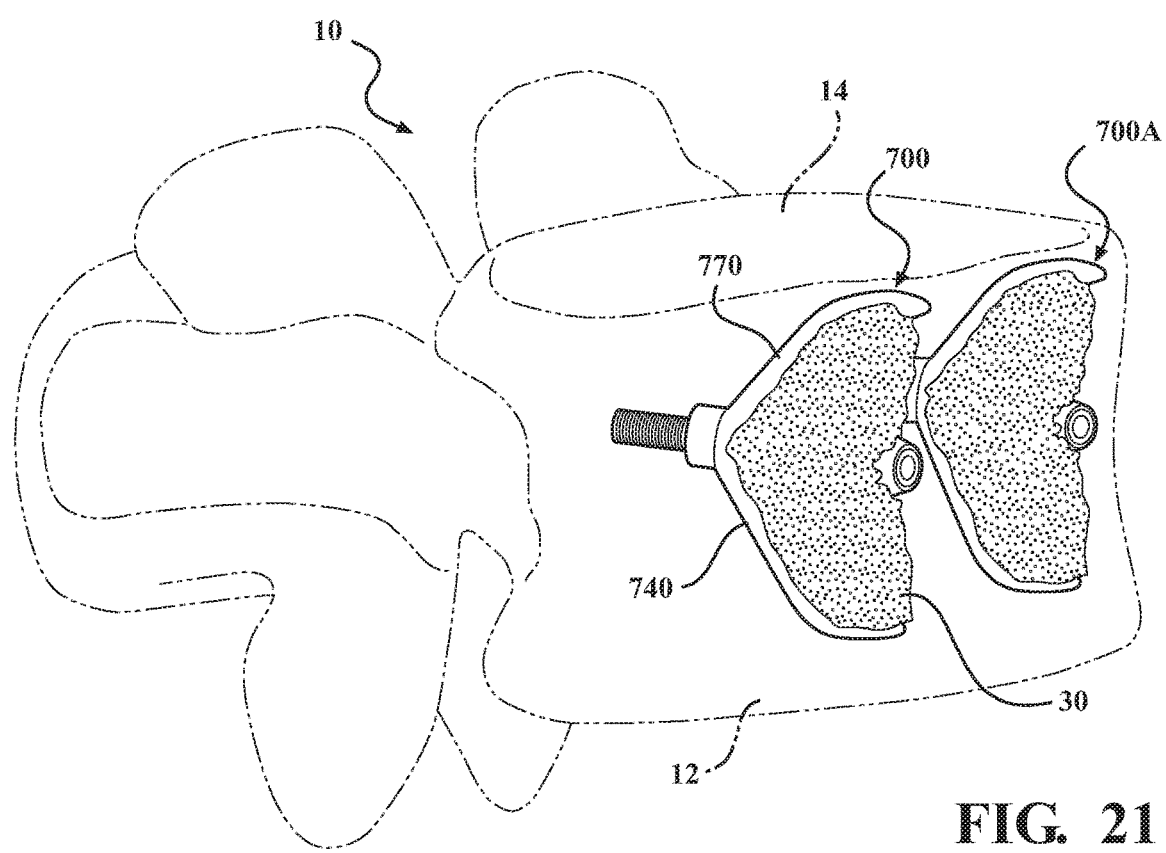
FIG. 21 depicts a step in a method of placing a pair of implants into a bone according to one implementation of the disclosure

In yet another variant of the method, the implant 700 is used for a bone repair. Implant is inserted into the vertebra and caused to be expanded as described in other implementations herein. However, because implant 700 includes the upper blade 770 and the lower blade 740, either one or both blades may bend if contact is made with either top plate 14 or bottom plate 12 of vertebra 10. When implant 700 is expanded in vertebra 10 as shown in FIG. 21, both upper blade 770 and lower blade 740 bend upon contacting top and bottom plates 14, 12, respectively, and accordingly, the vertebra is not punctured. In this implementation, a second implant 700A is also implanted and expanded in the same manner as implant 700, preferably simultaneously. As with the other methods previously described, cement 30 is injected into the void created through the expansion of the implant, as shown in FIG. 21.

In any of the above method implementations, two implants may be inserted and expanded within a single vertebra or other bone, similarly to that shown for implants 700 in FIG. 21. Each implant may be positioned relative to the other within the vertebra to maximize restoration of the vertebra when expanded.

Although the disclosure herein has been described with reference to particular implementations, it is to be understood that these implementations are merely illustrative of the principles and applications of the present disclosure. It is therefore to be understood that numerous modifications may be made to the illustrative implementations and that other arrangements may be devised without departing from the spirit and scope of the present disclosure as defined by the appended claims.

The invention claimed is:

1. An expandable implant for bone restoration comprising:
   a first end element;
   a second end element, the second end element positioned such that a longitudinal axis of the implant is defined through a center of the first end element and a center of the second end element;
   a plate movable in a first direction;
   a blade movable in a second direction, the blade comprising a base and a tip;
   a first interconnecting element extending between the plate and at least one of the first end element and the second end element; and
   a second interconnecting element comprising a material web extending between the base of the blade and at least one of the first end element and the second end element,
   wherein the implant is configured to be expanded from a collapsed position in which the blade is substantially parallel to the longitudinal axis, to an expanded position in which the material web of the second interconnecting element plastically deforms with the blade being non-parallel to the longitudinal axis.

2. The implant of claim 1, wherein the first interconnecting element comprises a first arm extending between the plate and the first end element and a second arm extending between the plate and the second end element, and wherein the second interconnecting element comprises a third arm extending between a base of the blade and the first end element and a fourth arm extending between the base of the blade and the second end element.

3. The implant of claim 2, wherein the blade is configured to pivot about a location on one of the third arm and the fourth arm.

4. The implant of claim 2, wherein the third arm and the fourth arm are configured to pivot relative to one another.

5. The implant of claim 1, wherein the plate and the blade are in a single plane in the collapsed position and in the expanded position.

6. The implant of claim 1, wherein the blade is configured to bend when subjected to a predetermined load.

7. The implant of claim 1, wherein the blade defines a recess across a width of the blade, the recess being closer to the tip than the base and functioning as a pivot point between portions of the blade on each side of the recess when the tip of the blade is subject to a load.

8. The implant of claim 1, wherein the blade comprises a planar bottom surface.

9. The implant of claim 1, wherein the tip of the blade is bulbous.

10. The implant of claim 1, wherein the tip of the blade is farther from the longitudinal axis than the plate with the implant in the expanded position, and wherein the tip of the blade is farther from the longitudinal axis than the base of the blade in the expanded position.

11. An expandable implant for bone restoration comprising:
   a first end element;
   a second end element, the second end element positioned such that a longitudinal axis of the implant is defined the first end element and the second end element;
   a plate movable in a first direction;
   a blade movable in a second direction, the blade comprising a base and a tip;
   a first arm extending between the plate and the first end element;
   a second arm extending between the plate and the second end element;
   a third arm extending between the base of the blade and the first end element; and
   a fourth arm extending between the base of the blade and the second end element,
   wherein the implant is configured to be expanded from a collapsed position in which the blade is substantially parallel to the longitudinal axis, to an expanded position in which the blade is non-parallel to the longitudinal axis, wherein at least one of the third arm and the fourth arm comprises a material web configured to plastically deform with the implant in the expanded position.

12. The implant of claim 11, wherein the third arm and the fourth arm are angled relative to one another with the implant in the expanded position.

13. The implant of claim 11, wherein the tip of the blade is configured to move in an arcuate manner to displace or cut soft tissue within the bone and create a cavity.

14. The implant of claim 11, wherein the blade is configured to bend when subjected to a predetermined load.

15. The implant of claim 11, wherein the tip of the blade is bulbous.

16. An expandable implant for bone restoration comprising:
    a first end element;
    a second end element, the second end element positioned such that a longitudinal axis of the implant is defined through a center of the first end element and a center of the second end element;
    a plate movable in a first direction;
    a blade movable in a second direction, the blade comprising a base and a tip;
    a first interconnecting element extending between the plate and at least one of the first end element and the second end element; and
    a second interconnecting element extending between the base of the blade and at least one of the first end element and the second end element,
    wherein the implant is configured to be expanded from a collapsed position in which the blade is substantially parallel to the longitudinal axis, to an expanded position in which both the base and the tip of the blade move in an arcuate manner such that the blade is non-parallel to the longitudinal axis,
    wherein the implant is configured to undergo plastic deformation during expansion such that the blade is preventing from returning to the collapsed position.

17. The implant of claim 16, wherein the blade is configured to bend when subjected to a predetermined load.

18. The implant of claim 16, wherein the tip of the blade is bulbous.

\* \* \* \* \*